(12) United States Patent
Felgner et al.

(10) Patent No.: US 7,319,012 B2
(45) Date of Patent: Jan. 15, 2008

(54) PROTEIN ARRAYS AND METHODS AND SYSTEMS FOR PRODUCING THE SAME

(75) Inventors: Philip L. Felgner, Rancho Santa Fe, CA (US); Denise L. Doolan, Rockville, MD (US)

(73) Assignee: Gene Therapy Systems, Inc., San Diego, CA (US)

( * ) Notice: Subject to any disclaimer, the term of this patent is extended or adjusted under 35 U.S.C. 154(b) by 544 days.

(21) Appl. No.: 10/159,428

(22) Filed: May 29, 2002

(65) Prior Publication Data

US 2003/0082579 A1 May 1, 2003

Related U.S. Application Data

(60) Provisional application No. 60/294,739, filed on May 30, 2001.

(51) Int. Cl.
*G01N 33/53* (2006.01)
*C12Q 1/70* (2006.01)
*C12Q 1/68* (2006.01)
*C40B 30/04* (2006.01)

(52) U.S. Cl. .............. 435/7.2; 435/5; 435/6; 435/7.1; 435/7.32; 435/DIG. 3; 435/DIG. 15; 435/DIG. 17

(58) Field of Classification Search ............. 435/5, 435/6, 724, 7.2, 7.1, 7.32, DIG. 3, DIG. 15, 435/DIG. 17
See application file for complete search history.

(56) References Cited

U.S. PATENT DOCUMENTS

| | | | |
|---|---|---|---|
| 4,683,202 A | | 7/1987 | Mullis |
| 4,965,188 A | | 10/1990 | Mullis et al. |
| 5,478,726 A | * | 12/1995 | Shinnick et al. ............ 435/7.24 |
| 5,733,731 A | * | 3/1998 | Schatz et al. ................. 435/6 |
| 5,874,409 A | * | 2/1999 | Victoria et al. ................ 514/15 |
| 5,888,736 A | | 3/1999 | Lacroix et al. |
| 6,043,045 A | * | 3/2000 | Hoch et al. .................... 435/17 |
| 6,063,571 A | | 5/2000 | Uhlmann et al. |
| 6,083,695 A | | 7/2000 | Hardin et al. |
| 6,280,977 B1 | * | 8/2001 | Liang et al. ................ 435/91.2 |
| 6,291,665 B1 | | 9/2001 | Gaffney et al. |
| 6,936,470 B2 | | 8/2005 | Liang et al. |

FOREIGN PATENT DOCUMENTS

| | | |
|---|---|---|
| WO | WO99/57312 A1 | 11/1999 |
| WO | WO 00/34512 A1 | 6/2000 |
| WO | WO 00/56914 A1 | 9/2000 |
| WO | WO 01/83827 A1 | 11/2001 |
| WO | WO 01/94944 A2 | 12/2001 |
| WO | WO 02/068682 A2 | 9/2002 |
| WO | WO 02/083871 A2 | 10/2002 |

OTHER PUBLICATIONS

Felgner et al., Nature Biotechnology Apr. 1999, vol. 17: 329-330.*
Sykes et al., Nature Biotechnology, Apr. 1999, vol. 17: 355-359.*
Meloen et al., J. Molecular Recognition, Nov./Dec. 2000, vol. 13: 352-359.*
International Search Report, International Application No. PCT/US02/17005, International Filing Date May 29, 2002.
Fraser et al., "Genomic sequence of a Lyme disease spirochaete, Borrelia burgdorferi", Nature, vol. 390, pp. 580-586, Dec. 11, 1997.
Tomb et al., "The complete genome sequence of the gastric pathogen Helicobacter pylori", Nature, vol. 388, pp. 539-547, Aug. 7, 1997.
Read et al., "Genome sequences of Chlamydia trachomatis MoPn and Chlamydia pneumoniae AR39", Nucleic Acids Research, vol. 28, No. 6, pp. 1397-1406, 2000.
Nierman et al., "Complete genome sequence of *Caulobacter crescentus*", PNAS, vol. 98, No. 7, pp. 4136-4141, Mar. 27, 2001.
Casjens et al., "A bacterial genome in flux: the twelve linear and nine circular extrachromosomal DNAs n an infectious isolate of the Lyme disease spirochete *Borrelia burgdorferi*", Molecular Microbiology 35(3), pp. 490-516, 2000.
Fraser et al., Complete Genome Sequence of Treponema pallidum, the Syphilis Spirochete, Science, vol. 281, pp. 375-388, Jul. 17, 1998.
Bult et al., "Complete Genome Sequence of the Methoanogenic Archaeon, *Methanococcus jannaschii*", Science, vol. 273, pp. 1058-1073, Aug. 23, 1996.
Gardner et al., "Chromosome 2 Sequence of the Human Malaria Parasite Plasmodium falciparum", Science, vol. 282, pp. 1126-1132, Nov. 6, 1998.
Tettelin et al., "Complete Genome Sequence of Neisseria meningitidis Serogroup B Strain MC58", Science, vol. 287, pp. 1809-1815, Mar. 10, 2000.
Fraser et al., "The Minimal Gene Complement of *Mycoplasma genitalium*", Science, vol. 270, pp. 397-403, Oct. 20, 1995.
He et al., "High Throughput Protein Expression and Immunological Screening for Novel Vaccinia Virus Antigens by Vaccinomics Platform Technology", 3rd Annual American Society for Microbiology (ASM) Biodefense Research Meeting, Baltimore, MD, Mar. 20-23, 2005.
He et al., "High Throughput Screening for Novel Tuberculosis Vaccine Antigens by Vaccinomics Technology" Vaccines—All Things Considered, sponsored by GTCbio, Burlingame, California, Dec. 2-3, 2004.
Cole et al., "Massive gene decay in the leprosy bacillus", Nature, vol. 409, pp. 1007-1011, Feb. 22, 2001.
Cole et al., "Deciphering the biology of *Mycobacterium tuberculosis* from the complete genome sequence", Nature, vol. 393, pp. 537-544, Jun. 11, 1998.

(Continued)

*Primary Examiner*—Mark L. Shibuya
(74) *Attorney, Agent, or Firm*—Knobbe Martens Olson & Bear LLP

(57) ABSTRACT

Methods of rapidly generating and analyzing a plurality of polypeptides are disclosed. More specifically, libraries and arrays of polypeptides are assayed in order to determine their individual immunogenic effect. Based on the immunogenic effect of polypeptides, specific subunit vaccines can be developed.

18 Claims, 11 Drawing Sheets

OTHER PUBLICATIONS

Cole et al., "Deciphering the biology of *Mycobacterium tuberculosis* from the complete genome sequence", Nature, vol. 396, pp. 190-198, Nov. 12, 1998.

Parkhill et al., "Complete DNA sequence of a serogroup A strain of Neisseria meningitidis Z2491", Nature, vol. 404, pp. 502-506, Mar. 30, 2000.

Parkhill et al., "The genome sequence of the food-borne pathogen *Campylobacter jejuni* reveals hypervariable sequences", Nature, vol. 403, pp. 665-668, Feb. 10, 2000.

Heldelberg et al., "DNA sequence of both chromosomes of the cholera pathogen Vibrio cholerae", Nature, vol. 406, pp. 477-484, Aug. 3, 2000.

Nelson et al., "Evidence for lateral gene transfer between Archaea and Bacteria from genome sequence of Thermotoga maritima", Nature, vol. 399, pp. 323-329, May 27, 1999.

Klenk et al., "The complete genome sequence of thy hyperthermophilic, sulphate-reducing archaeon Archaeoglobus fulgidus", Nature, vol. 390, pp. 364-370, Nov. 27, 1997.

White et al., "Genome Sequence of the Radioresistant Bacterium Deinococcus radiodurans R1", Science, vol. 286, pp. 1571-1577, Nov. 19, 1999.

Fleischmann et al., "Whole-Genome Random Sequencing and Assembly of Haemophilus Influenzae Rd", Science, vol. 269, pp. 496-512, Jul. 28, 1995.

Goebel et al., "The Complete DNA Sequence of Vaccinia Virus", Virology, vol. 179, No. 1, pp. 247-266, Nov. 1990. (XP-000253545).

Hartley et al, "DNA Cloning Using In Vitro Site-Specific Recombination", Genome Research, vol. 10, pp. 1788-1795, Nov. 2000. (XP-002187669).

Hudson et al., "The Complete Set of Predicted Genes from *Saccharomyces cerevisiae* in Readily Usable Form", Genome Research, vol. 7, pp. 1169-1173, Dec. 1997. (XP-002127444).

Kain et al., "Universal Promoter for Gene Expression Without Cloning: Expression-PCR", Bio Techniques, vol. 10, No. 3, 1991. (XP-00912135).

Cassata, et al. Rapid expression screening of *Caenorhabditis elegans* homebox open reading frames using a two-step polymerase chain reaction promoter-*gfp* reporter construction technique.

Delcher, et al. "Improved microbial gene identification with GLIMMER." Nucleic Acids Res. 27:4636-4641 (1999).

Furth, et al. "Temporal control of gene expression in transgenic mice by a tetracycline-responsive promoter." Proc. Natl. Acad. Sci. 91:9302-6 (1994).

Goodchild, J. "Conjugates of Oligonucleotides and Modified Oligonucleotides: A Review of their Synthesis and Properties." Bioconjugate Chemistry. 1(3):166-187 (May/Jun. 1990).

Ido, et al. "Construction of T-Tailed Vectors Derived fro a pUC Plasmid: a Rapid System Direct Cloning of Unmodified PCR Products." Biosci. Biotech. Biochem. 61(10):1776-1767 (1997).

No, et al. "Ecdysone-inducible gene expression in mammalian cells and transgenic mice." Proc. Natl. Acad. Sci. 93:3346-51 (1996).

Prodromou, et al. "PROTOCOL, Recurvise PCR: a novel technique for total gene synthesis." Protein Engineering. 5(8):827-829 (1992).

Salzberg, et al. "Microbial gene identification using interpolated Markov models." Nucleic Acids Res. 26:544-548 (1998).

Seed, B. "Purification genomic sequences from bacteriophage libraries by recombination and selection *in vivo*." Nucleic Acids Research 11(8):2427-2445 (1983).

Sykes, et al. "Linear expression elements: a rapid, in vivo, method to screen for gene functions." Nature Biotechnology. 17:355-359 (1999).

Zhang, et al. A new logic for DNA engineering using recombination in *Exherichia coli*. Nature Genetics. 20:123-128 (1998).

Zhang, et al. "DNA Cloning by Homologous Recombination in *Eschenichia coli*." Nature Biotechnology. 18:1314-1317 (2000).

* cited by examiner

Step 1  Synthesize gene-specific custom primers containing the universal TAP ends 5' and 3' -Custom Oligos Step 2  Amplify the gene-of-interest with the custom primers to create the TAP Primary Fragment Step 3

This fragment is transcriptionally active ready for transfection into cultured cells, or injection into animals

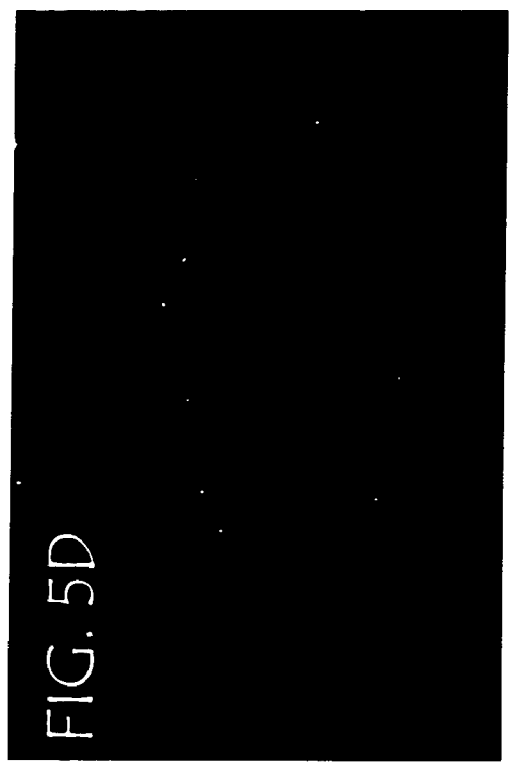
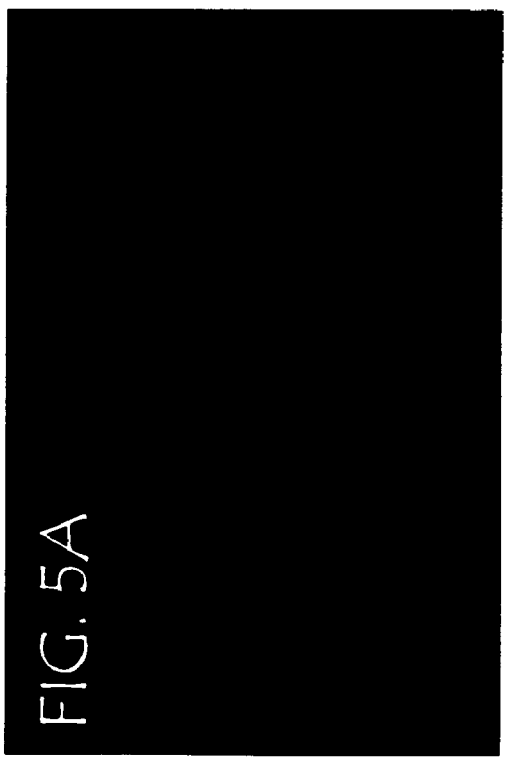
FIG. 5A
FIG. 5B
FIG. 5C
FIG. 5D

SEQUENCE LISTING

```
<160> NUMBER OF SEQ ID NOS: 5

<210> SEQ ID NO 1
<211> LENGTH: 69
<212> TYPE: DNA
<213> ORGANISM: Homo Sapiens

<400> SEQUENCE: 1
atggatgcaa tgaagagagg gctctgctgt gtgctgctgc tgtgtggagc agtcttcgtt      60
tcgcccagc                                                             69

<210> SEQ ID NO 2
<211> LENGTH: 17
<212> TYPE: DNA
<213> ORGANISM: Artificial Sequence
<220> FEATURE:
<223> OTHER INFORMATION: HA epitope encoding sequence added to a pCMVm
      5' promoter sequence

<400> SEQUENCE: 2
ccgccatgtt gacattg                                                    17

<210> SEQ ID NO 3
<211> LENGTH: 64
<212> TYPE: DNA
<213> ORGANISM: Artificial Sequence
<220> FEATURE:
<223> OTHER INFORMATION: HA epitope encoding sequence attached to a
      pCMVm 3' promoter sequence

<400> SEQUENCE: 3
ggcagatctg ggaggctagc gtaatccgga acatcgtatg ggtacattgt taagtcgacg      60
gtgc                                                                  64

<210> SEQ ID NO 4
<211> LENGTH: 56
<212> TYPE: DNA
<213> ORGANISM: Artificial Sequence
<220> FEATURE:
<223> OTHER INFORMATION: HA epitope encoding sequence added to a pTP-
      SV40 5' terminator sequence

<400> SEQUENCE: 4
gatcccgggt acccatacga tgttccggat tacgcttagg ggagatctca gacatg         56

<210> SEQ ID NO 5
<211> LENGTH: 32
<212> TYPE: DNA
<213> ORGANISM: Artificial Sequence
```

```
-continued

<220> FEATURE:
<223> OTHER INFORMATION: HA epitope encoding sequence added to a pTP-
      SV40 3' terminator sequence

<400> SEQUENCE: 5
caggatatca tgcctgcagg acgactctag ag                                      32
```

US 7,319,012 B2

PROTEIN ARRAYS AND METHODS AND SYSTEMS FOR PRODUCING THE SAME

RELATED APPLICATIONS

This application claims priority from U.S. Provisional Application 60/294,739 filed on May 30, 2001.

STATEMENT OF GOVERNMENT INTEREST

The U.S. Government has a non exclusive, irrevocable, paid up license to practice the invention or to have the invention practiced throughout the world by or on behalf of the Government as provided under the terms of CRADA NCRADA-NMR-01-1037 through the Naval Medical Research Center.

BACKGROUND OF THE INVENTION

1. Field of the Invention

The present invention relates to methods of rapidly generating and analyzing a plurality of polypeptides. More specifically, polypeptides can be assayed to determine their individual immunogenic effect. Monitoring the immunogenic effect of polypeptides allows skilled artisans to develop specific subunit vaccines.

2. Description of the Related Art

Traditional vaccine technology suffers from the problem that it often produces various degrees of reactogenicity in different hosts. In light of general health concerns and the growing threat of bioterrorism, there is a need to develop subunit vaccines capable of inducing an appropriate immune response in the context of multiple, and genetically diverse hosts. This approach requires the identification of a number of specific antigenic polypeptides. One of the most difficult tasks in developing a vaccine, or any recombinant subunit vaccine, is the identification of the antigens that can stimulate the most effective immune response against a particular pathogen, especially when the genome of the pathogen is large.

As an example, Smallpox, because of its high case-fatality rates and transmissibility, now represents one of the most serious bioterrorist threats. Over the centuries, naturally occurring Smallpox, with its case-fatality rate of 30 percent or more and its ability to spread in any climate and season, has been universally feared as the one of the most devastating of all the infectious diseases. The use of Vaccinia virus as a vaccine enabled the global eradication of naturally occurring Smallpox. The last naturally occurring case of Smallpox occurred in Somalia in 1977. In May 1980, the World Health Assembly certified that the world was free of naturally occurring Smallpox. Routine vaccination in the United States ended in 1971, and except for some soldiers and laboratory workers, nobody has been vaccinated since 1983. However, due to the present threat of Smallpox being used as a weapon of terrorism, large-scale vaccination may once again be coming to the forefront.

Unfortunately, the use of Vaccinia virus as a Smallpox vaccine has, throughout the Smallpox eradication campaign until the cessation of vaccination in the civilian population in the 1980s, been manufactured using 25 year-old technology. This technology comprises the harvesting of virus-containing material from live vaccinifers. Despite the proven safety record of this method of manufacture, various degrees of reactogenicity have been reported in vaccine recipients. In the current age, when mass vaccination might be an important aim yet immunosuppressive diseases are perhaps more prevalent than ever, a vaccine without the infective properties of a live virus is more critical than ever. An understanding of the full spectrum of a pathogen's immunostimulatory polypeptides would be a key starting point to developing more effective vaccines.

SUMMARY OF THE INVENTION

Embodiments of the invention relate to methods of generating a library of target organism polypeptides. The methods can include the steps of: (a) performing a first PCR reaction using a first primer pair capable of amplifying a desired polynucleotide sequence from the target organism to provide an amplified coding sequence, which amplified coding sequence is not transcriptionally active; (b) providing a second PCR nucleotide primer pair capable of adding at least one nucleotide sequence that confers transcriptional activity to the amplified coding sequence; (c) performing a second PCR reaction with the second primer pair and the amplified coding sequence, thereby resulting in amplification of a transcriptionally active coding sequence; (d) expressing the polypeptide of the transcriptionally active coding sequence; and (e) repeating steps (a)–(d) at least 10 times, with different first primer pairs to express different polypeptides of said target organism. In other embodiments, steps (a)–(d) can be repeated at least, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more times, with different first primer pairs to express different polypeptides of said target organism.

The methods of generating a library of target organism polypeptides can further include adding at least one polynucleotide sequence operably encoding a linker molecule to the amplified coding sequence or the transcriptionally active coding sequence, wherein the linker molecule immobilizes the polypeptide to a solid support. In other embodiments, expressing the transcriptionally active coding sequence and the polynucleotide sequence operably encoding a linker molecule produces a target organism polypeptide attached to a linker molecule. In one embodiment, the linker molecule can be an epitope, for example, a HA epitope. Other linker molecules include, for example, a 6x, 7x, 8x, 9x, or 10x histidine tag, GST tag, fluorescent protein tag, Flag tag, and the like.

In other embodiments, the at least one sequence that confers transcriptional activity is a promoter sequence, a terminator sequence and the like.

Other embodiments relate to automated systems that are capable of performing the methods discussed herein. For example, an automated system can be used to design the first primer pair, perform the first PCR reaction, perform the second PCR reaction, express the transcriptionally active coding sequence, and the like.

Still further embodiments of the invention relate to methods of screening a library of target organism polypeptides in order to identify a target organism antigen that is capable of eliciting a humoral immune response. The methods can include providing a library of target organism polypeptides attached to a linker molecule; immobilizing at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more polypeptides to a solid support; and assaying the polypeptides with at least one antibody from an animal that has been immunized with one or more antigens from the target organism to identify a target organism antigen capable of eliciting a humoral immune response.

Additional embodiments relate to methods of screening a library of target organism polypeptides in order to identify a target organism antigen that is capable of eliciting a cell-mediated immune response. The methods can include, for example, providing a library of target organism polypeptides; delivering at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more target organism polypeptides into a plurality of antigen-presenting cells; and assaying the antigen-presenting cells with at least one T-cell from an animal that has been immunized with one or more antigens from the target organism to identify a target organism antigen capable of eliciting a cell-mediated immune response. In certain embodiments, the antigen-presenting cells can be B cells, macrophages, dendritic cells, and the like.

Other embodiments relate to methods of developing a subunit vaccine against a target organism. The methods can include providing a target organism antigen that is capable of eliciting a humoral immune response; administering the antigen to a subject alone or in combination with at least one other target organism antigen that is capable of eliciting an immune response to a subject; and monitoring the generation of an immune response to the antigen or combination of the antigens in the subject.

In other embodiments, subunit vaccines against a target organism can also be developed by providing a target organism antigen that is capable of eliciting a cell-mediated immune response. Methods can include administering the antigen to a subject alone or in combination with at least one other target organism antigen that is capable of eliciting an immune response to a subject; and monitoring the generation of an immune response to the antigen or combination of the antigens in the subject.

Still further embodiments relate to methods of developing a subunit vaccine against a target organism. The methods can include providing a nucleic acid sequence operably encoding a target organism antigen that has been identified as capable of eliciting a humoral immune response; introducing the nucleic acid sequence alone or in combination with at least one other nucleic acid that is capable of expressing a target organism antigen to a subject; and monitoring the generation of an immune response to the nucleic acid or combination of nucleic acids in the subject.

Further methods of developing a subunit vaccine against a target organism, can include providing a nucleic acid sequence operably encoding a target organism antigen that has been identified as capable of eliciting a cell-mediated immune response; introducing the nucleic acid sequence alone or in combination with at least one other nucleic acid that is capable of expressing a target organism antigen to a subject; and monitoring the generation of an immune response to the nucleic acid or combination of nucleic acids in the subject.

Other embodiments of the invention relate to arrays of at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more target organism polypeptides. The arrays can be used to screen target organism polypeptides in order to identify a target organism antigen that is capable of eliciting a cell-mediated immune response. The methods can include providing an array of target organism polypeptides; delivering at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more of the target organism polypeptides into a plurality of antigen-presenting cells; and assaying the antigen-presenting cells with at least one T-cell from an animal that has been immunized with one or more antigens from target organism to identify a target organism antigen capable of eliciting a cell-mediated immune response. The antigen-presenting cells can be B cells, macrophages, dendritic cells, and the like.

Further embodiments also relate to arrays of at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more target organism polypeptides attached to a linker molecule. The arrays can be used to screen target organism polypeptides in order to identify a target organism antigen that is capable of eliciting a humoral immune response. The methods can include providing an array of target organism polypeptides attached to a linker molecule; immobilizing at least 10 of the target organism polypeptides to a solid support; and assaying the polypeptides with at least one antibody from an animal that has been immunized with one or more antigens from the target organism to identify a target organism antigen capable of eliciting a humoral immune response.

Additional embodiments relate to arrays including a plurality of individual locations, wherein a different polypeptide from a target organism is positioned at each location, and wherein at least about 50%, 60%, 70%, 75%, 80%, 85%, 90%, 95% or 100% of all expressed polypeptides from the target organism are positioned on the array. Arrays can include different, expressed polypeptides from any target organism. In certain embodiments of the invention Vaccinia virus is the target organism. In other embodiments, the target organism can be a pathogen including for example, *B. anthracis, Clostridium botulism, Yersinia pestis, Variola major, Francisella tularensis, P. falciparum, Streptococcus, Borrelia burgdorferi, Chlamydia trachomatis, Helicobacter pylori, Mycobacterium tuberculosis*, causative pathogens of viral hemorrhagic fevers, Ebola, Marburg, pox viruses, Arenaviruses, LCM, Junin virus, Machup virus, Guanarito virus, Bunyaviruses, Hantaviruses, Flaviruses, Dengue virus, Filoviruses, *Coxiella burnetti, Brucella* species, *Burkholderia mallei, Ricinus communis, Clostridium perfringens, Staphylococcus, Rickettsia prowazekii* and other *Rickettsias*, Food and Waterborne Pathogens, Diarrheagenic *E. coli*, Pathogenic Vibrios, *Shigella* species, *Salmonella, Listeria monocytogenes, Campylobacter jejuni, Yersinia enterocolitica*, Caliciviruses, Hepatitis A Protozoa, *Cryptosporidium parvum, Cyclospora cayatanensis, Giardia lamblia, Entamoeba, histolytica,* Toxoplasma, Microsporidia, Viral encephalitides, West Nile Virus, LaCrosse virus, VEE, EEE, WEE, Japanese Encephalitis Virus, Kysanur Forest Virus, Nipah virus, Tickborne hemorrhagic fever viruses, Crimean-Congo Hemorrhagic fever virus, Tickborne encephalitis viruses, Multi-drug resistant TB, Rabies virus, Rift Valley Fever virus, Lassa Fever virus, Influenza virus, and Yellow fever virus, and the like. Polypeptides in the arrays can be positioned in numerous ways, including, for example, being suspended in solution, or bound to the array. Furthermore, the positioned polypeptides can be attached to a linker molecule, selected from the group consisting of, for example, a 6×, 7×, 8×, 9×, or 10× histidine tag, GST tag, fluorescent protein tag, or Flag tag. Positioned polypeptides with linker molecules can be bound to arrays.

Further embodiments relate to methods of generating a library of target organism polypeptides which can include the following steps of: (a) PCR cloning a desired nucleic acid coding sequence from the target organism into a vector by flanking the coding sequence with first and second adapter sequences, wherein the first and second adapter sequences; (b) contacting the coding sequence with the vector having sequences homologous to the first and second adapter sequences within a host cell under conditions such that the coding sequence is incorporated into the vector by recombination in vivo in the host cell; (c) expressing the polypeptide encoded by the coding sequence; and (d) repeating steps (a)–(c) at least 10 times, with different coding sequences to express different polypeptides of said target organism.

In other embodiments, steps (a)–(c) can be repeated at least, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more times, with different coding sequences to express different polypeptides of said target organism.

The target organism can be a pathogen including for example, *B. anthracis, Clostridium botulism, Yersinia pestis, Variola major, Francisella tularensis, P. falciparum, Streptococcus, Borrelia burgdorferi, Chlamydia trachomatis, Helicobacter pylori, Mycobacterium tuberculosis*, causative pathogens of viral hemorrhagic fevers, Ebola, Marburg, pox viruses, Arenaviruses, LCM, Junin virus, Machup virus, Guanarito virus, Bunyaviruses, Hantaviruses, Flaviruses, Dengue virus, Filoviruses, *Coxiella burnetti, Brucella* species, *Burkholderia mallei, Ricinus communis, Clostridium perfringens, Staphylococcus, Rickettsia prowazekii* and other *Rickettsias*, Food and Waterborne Pathogens, Diarrheagenic *E. coli*, Pathogenic Vibrios, *Shigella* species, *Salmonella, Listeria monocytogenes, Campylobacter jejuni, Yersinia enterocolitica*, Caliciviruses, Hepatitis A Protozoa, *Cryptosporidium parvum, Cyclospora cayatanensis, Giardia lamblia, Entamoeba, histolytica,* Toxoplasma, Microsporidia, Viral encephalitides, West Nile Virus, LaCrosse virus, VEE, EEE, WEE, Japanese Encephalitis Virus, Kysanur Forest Virus, Nipah virus, Tickborne hemorrhagic fever viruses, Crimean-Congo Hemorrhagic fever virus, Tickborne encephalitis viruses, Multi-drug resistant TB, Rabies virus, Rift Valley Fever virus, Lassa Fever virus, Influenza virus, and Yellow fever virus, and the like.

Additional methods relate to adding at least one polynucleotide sequence operably encoding a linker molecule to the nucleic acid coding sequence from the target organism, wherein the linker molecule immobilizes the expressed polypeptide to a solid support. Furthermore, methods of expressing the desired nucleic acid coding sequence and the polynucleotide sequence operably encoding a linker molecule produces a target organism polypeptide attached to a linker molecule are also embodied.

Further methods relate to screening a library of target organism polypeptides in order to identify a target organism antigen that is capable of eliciting a humoral immune response, and can include: providing a library of target organism polypeptides attached to a linker molecule; immobilizing at least 10 of the target organism polypeptides to a solid support; and assaying the polypeptides with at least one antibody from an animal that has been immunized with one or more antigens from the target organism to identify a target organism antigen capable of eliciting a humoral immune response.

Further embodiments relate to methods of screening a library of target organism polypeptides in order to identify a target organism antigen that is capable of eliciting a cell-mediated immune response, including: providing a library of target organism polypeptides; delivering at least 10 of the target organism polypeptides into a plurality of antigen-presenting cells; and assaying the antigen-presenting cells with at least one T-cell from an animal that has been immunized with one or more antigens from the target organism to identify a target organism antigen capable of eliciting a cell-mediated immune response Additional methods relate to generating a library of target organism polypeptides, which can include the following steps: (a) amplifying a desired polynucleotide coding sequence from the target organism by performing PCR with a first primer pair capable of amplifying the desired polynucleotide coding sequence; (b) expressing the amplified polynucleotide coding sequence; and repeating steps (a)–(b) at least 10 times, with different first primer pairs to express different polypeptides of said target organism.

The PCR reaction can include: (a) performing a first PCR reaction using a first primer pair capable of amplifying a desired polynucleotide sequence from the target organism to provide an amplified coding sequence, which amplified coding sequence is not transcriptionally active; (b) providing a second PCR nucleotide primer pair capable of adding at least one nucleotide sequence that confers transcriptional activity to the amplified coding sequence; (c) performing a second PCR reaction with the second primer pair and the amplified coding sequence, thereby resulting in amplification of a transcriptionally active coding sequence.

BRIEF DESCRIPTION OF THE DRAWINGS

FIG. 5. demonstrates that fluorescent proteins (goat IgG antibody) can be more effectively delivered into either NIH-3T3 cells (A&B) and human dendritic cells (C&D) with a protein delivery reagent (B&D) as opposed to without a protein delivery reagent (A&C).

FIG. 12. illustrates DNA templates encoding three antigens from the malaria parasite that were amplified using custom oligos specific to each gene with common 5' and 3' TAP ends. The second PCR reaction was carried out to append the TAP promoter and TAP terminator to each primary TAP product, adding an additional 1050 bp in size, to produce the final active TAP Expression Fragments. The samples were separated by electrophoresis on 0.8% agarose gel with the corresponding primary and final PCR products running next to each other.

DETAILED DESCRIPTION OF THE PREFERRED EMBODIMENT

Overview

Figure 1:
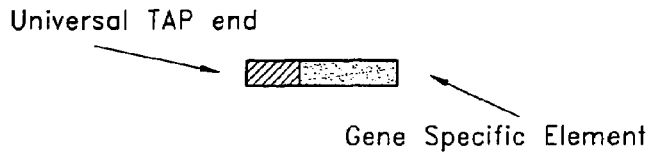
FIG. 1. illustrates one method used to generate TAP Expression Fragments.
Figure 1:
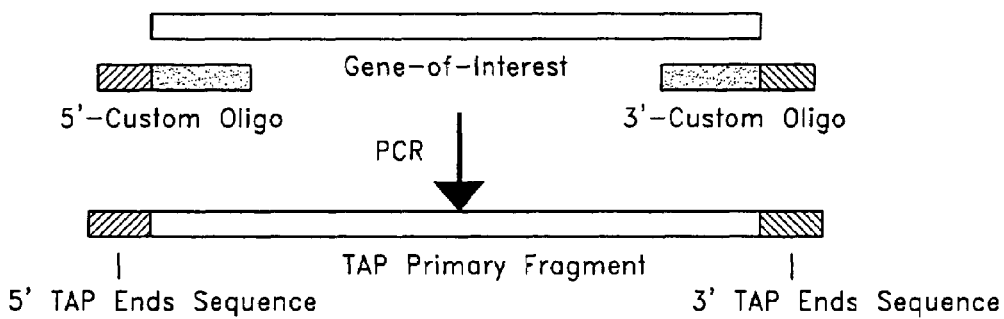
Figure 1:
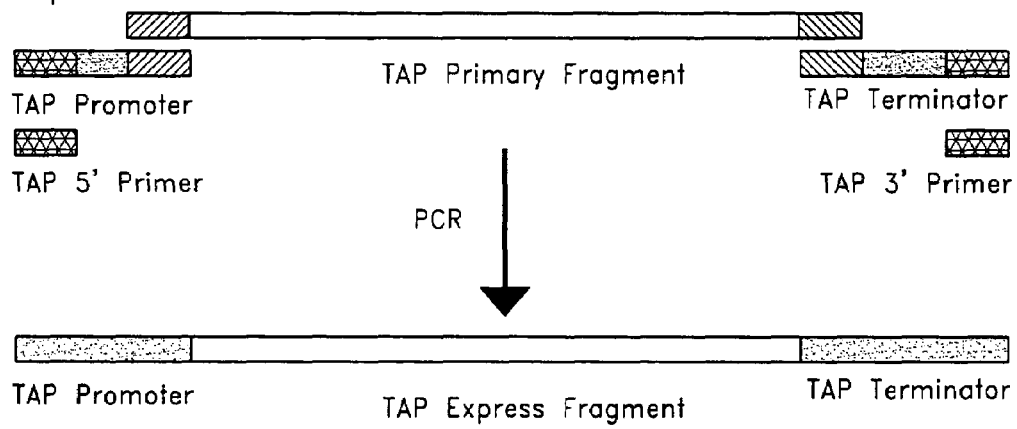

The present invention generally relates to methods of generating polypeptide libraries of a target organism, methods of monitoring the immunogenic effect of these polypeptides, methods of developing subunit vaccines, pharmaceutical compositions, and immunogenic compositions against the target organism based on the identification of antigenic polypeptides, and systems related to the same. In addition, this invention is directed to arrays of polypeptides that are derived from particular target organisms. Furthermore, the present invention is directed to an automated system capable of expressing polypeptides encoded by the target organism and determining the immunogenic effect of said polypeptides.

Polypeptide Libraries

Target Organisms

The term "target organism" is to be construed broadly and encompasses any prokaryotic or eucaryotic organism or cell, including mammals such as humans and other primates or domestic animals, bacteria, fungus, protozoa, viruses, and the like. In certain embodiments, the target organism can be a pathogen with a relatively large genome. Examples of target organisms include Vaccinia virus, *B. anthracis, Clostridium botulism, Yersinia pestis, Variola major, Francisella tularensis, P. falciparum, Streptococcus, Borrelia burgdorferi, Chlamydia trachomatis, Helicobacter pylori, Mycobacterium tuberculosis,* causative pathogens of viral hemorrhagic fevers, Ebola, Marburg, pox viruses, Arenaviruses, LCM, Junin virus, Machup virus, Guanarito virus, Bunyaviruses, Hantaviruses, Flaviruses, Dengue virus, Filoviruses, *Coxiella burnetti, Brucella* species, *Burkholderia mallei, Ricinus communis, Clostridium perfringens, Staphylococcus, Rickettsia prowazekii* and other *Rickettsias*, Food and Waterborne Pathogens, Diarrheagenic *E. coli*, Pathogenic Vibrios, *Shigella* species, *Salmonella, Listeria monocytogenes, Campylobacter jejuni, Yersinia enterocolitica*, Caliciviruses, Hepatitis A Protozoa, *Cryptosporidium parvum, Cyclospora cayatanensis, Giardia lamblia, Entamoeba, histolytica*, Toxoplasma, Microsporidia, Viral encephalitides, West Nile Virus, LaCrosse virus, VEE, EEE, WEE, Japanese Encephalitis Virus, Kysanur Forest Virus, Nipah virus, Tickborne hemorrhagic fever viruses, Crimean-Congo Hemorrhagic fever virus, Tickborne encephalitis viruses, Multi-drug resistant TB, Rabies virus, Rift Valley Fever virus, Lassa Fever virus, Influenza virus, and Yellow fever virus, and the like.

This invention can also be used to analyze cells that are effected by an autoimmune disease. By understanding the polypeptides coded by cells that are effected by autoimmune diseases, more effective treatments can be developed. A non-exclusive list of autoimmune diseases that can be analyzed with this invention include: Hashimoto's thyroiditis, pernicious anemia, Addison's disease, diabetes, rheumatoid arthritis, systemic lupus erythematosus, dermatomyositis, Sjogren's syndrome, lupus erythematosus, multiple sclerosis, myasthenia gravis, Reiter's syndrome, or Graves disease. Accordingly, in some embodiments a "target organism" can include cell types that are effected by a particular autoimmune disease. Additionally, a "target organism" can encompass abnormal cell types including cancerous cells, tumor cells, and diseased cells for example.

The term "polypeptide" is also to be construed broadly and is not limited to a specific number of amino acids in the encoded product. In some embodiments a "polypeptide" can be at least about 3, 4, 5, 6, 7, 8, or more amino acids long. A "polypeptide" according to the present invention encompasses, for example, naturally occurring polypeptides, recombinant polypeptides, peptides, oligopeptides, naturally occurring proteins, recombinant proteins, fragments, and variants or analogs of a polypeptide sequence and the like.

The term "array" is to be construed broadly, and includes any arrangement wherein a plurality of different polypeptides are held, presented, positioned, situated, or supported. Arrays can include microtiter plates, such as 48-well, 96-well, 144-well, 192-well, 240-well, 288-well, 336-well, 384-well, 432-well, 480-well, 576-well, 672-well, 768-well, 864-well, 960-well, 1056-well, 1152-well, 1248-well, 1344-well, 1440-well, or 1536-well plates, tubes, slides, chips, flasks, or any other suitable laboratory apparatus. Furthermore, arrays can also include a plurality of sub-arrays. A plurality of sub-arrays encompasses an array where more than one arrangement is used to position the target organism's polypeptides. For example, multiple 96-well plates could constitute a plurality of sub-arrays and a single array.

The term "library" is likewise to be construed broadly, and includes any non-natural collection of polypeptides, whether arranged or not. A library therefore encompasses an array but the two terms are not necessarily synonymous.

Embodiments of the invention encompass methods of generating polypeptide libraries from a particular target organism. The invention can be used to generate a plurality of polypeptides from any given target organism, with any particular sized genome. In other embodiments of the invention, the target organism can have more than 50 nucleotide coding sequences in its genome. In additional embodiments, the target organism can have a genome with more than: about 50, about 100, about 150, about 200, about 250, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more nucleotide coding sequences.

TAP Technology

Certain methods of the present invention are useful in quickly generating polypeptide libraries through the use of Transcriptionally Active Polymerase Chain Reaction ("TAP") fragments. With TAP technology, a particular gene of interest can be made transcriptionally active and ready for expression in less than one day for example. TAP fragments encompass transcriptionally active coding sequences, and the two terms can be used interchangeably. TAP fragments encompass polynucleotide fragments that can be readily transfected into animal cells or tissues by any nucleic acid transfection technique, without the need for subcloning into expression vectors and purification of plasmid DNA from bacteria. Transcriptionally active DNA fragments can be synthesized by polymerase chain reaction (PCR) amplification of any gene of interest using nested oligonucleotide primers and two DNA fragments, one of which comprises an active transcription promoter sequence and one of which comprises a basic transcription terminator element.

TAP fragments and methods of making the same are described in detail in U.S. Pat. No. 6,280,977, entitled "Method for generating transcriptionally active DNA fragments" which is hereby incorporated by reference in its entirety. In one embodiment, methods for creating TAP fragments can incorporate the steps of: i) oligonucleotide design ii) TAP primary fragment amplification, and iii) TAP expression fragment amplification. FIG. 1 illustrates one method for generating TAP fragments.

Creating TAP fragments involves designing custom oligonucleotide sequences. Primers complementary to the 5' and 3' ends of the gene of interest can be synthesized. The term "gene of interest" encompasses any "desired polynucleotide sequence" or "coding sequence," and can include any suitable number of nucleotides to permit amplification of the gene of interest. For example, the 5'-custom oligonucleotide can include about 41, 42, 43, 44, 45 and 46 nucleotides; of these, about 26 nucleotides comprise the 5'-TAP end universal sequence and about 15 to 20 nucleotides make up the gene-specific sequence. Accordingly, the gene-specific sequence can be, for example, about 15, 16, 17, 18, 19, or 20 nucleotides. The 5' oligonucleotide may also incorporate the Kozak consensus sequence (A/GC-CAUGG) around the start codon for more efficient translation of mRNA. In one embodiment, the start codon ATG can be included in the custom 5'-oligonucleotide. In another embodiment, the start codon ATG can be included in the custom 5'-oligonucleotide when the sequence encoding the peptide of interest lacks an initiation methionine codon on its 5' end.

The 3'-custom oligonucleotide can include any suitable number of nucleotides to permit amplification of the gene of interest. For example, the 3'-custom oligonucleotide can preferably contain about 35, 36, 37, 38, 39, 40, 41, 42, 43, 44, and 45 nucleotides; of these, about 20 nucleotides preferably comprise the 3'-TAP end universal sequence and about 20 nucleotides preferably are specific to the polynucleotide, or gene-of-interest. In still another embodiment, a complementary stop codon sequence, such as TCA, TTA, or CTA can be added to the end of the gene sequence to achieve proper translational termination of the expressed gene.

Another step in generating TAP fragments is to amplify the TAP primary fragment. The term "TAP primary fragment" encompasses an "amplified coding sequence," and in one embodiment relates to a polynucleotide sequence that has been amplified but is not transcriptionally active. This step involves performing PCR, which generates a polynucleotide fragment that contains the gene-of-interest with the added 5'- and 3'-TAP universal end sequences. These 5'- and 3'-TAP universal end sequences are useful for adding one or more nucleotide sequences that confer transcriptional activity. In one embodiment, these sequences can include TAP Express™ promoter and terminator fragments. Skilled artisans can adjust the above methods in order to optimize their particular PCR reaction, should the need arise.

A further step involves adding at least one polynucleotide sequence that confers transcriptional activity onto the TAP primary fragment. The end product of the $2^{nd}$ PCR reaction, termed a TAP expression fragment, is transcriptionally active DNA that can be used directly for in vivo, or in vitro, (e.g. cell-free) expression studies. In certain embodiments, TAP expression fragments can be transfected into cultured cells, or injected into animals. The term "TAP expression fragment" encompasses the term "transcriptionally active coding sequence".

Generating TAP fragments is a rapid and efficient way of making a large number of polynucleotide coding sequences transcriptionally active. Accordingly, embodiments include, a plurality of different genes from a target organism can be made transcriptionally active using TAP technology. In one embodiment, about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more genes are made transcriptionally active using TAP technology. As those with skill in the art can appreciate, a large plurality of different genes can be made transcriptionally active by repeating the disclosed methods the appropriate number of times.

Examples of polynucleotide sequences that confer transcriptional activity are promoter sequences, terminator sequences, binding sites for transcription factors, TATA box sequences, and enhancers. In one embodiment, one promoter and one terminator sequence are added onto the TAP fragment. These promoter and terminator sequences can be obtained in numerous ways. For example, using restriction enzyme digestion of commercially available plasmids and cDNA molecules, or they can be synthesized using an automated DNA synthesizer using methods well known in the art.

As used herein, the term "promoter" is a DNA sequence which extends upstream from the transcription initiation site and is involved in binding of RNA polymerase. The promoter may contain several short (<10 base pair) sequence elements that bind transcription factors, generally dispersed over >200 base pairs. A promoter that contains only elements recognized by general and upstream factors is usually transcribed in any cell type. Such promoters may be responsible for expression of cellular genes that are constitutively expressed (sometimes called housekeeping genes). There are also tissue-specific promoters limited to particular cell types, such as the human metallothionein (MT) promoter that is upregulated by heavy metal ions and glucocorticoids. The promoter can be selected based upon consideration of the desired use for the nucleic acid fragment. One skilled in the art can easily select an appropriate promoter according the uses of the nucleic acid fragment. For example, if the nucleic acid sequence encodes a gene with potential utility in human cells, then a promoter capable of promoting transcription in mammalian cells can be selected. Other examples of a promoter include a promoter from a plant or a plant pathogen, such as cauliflower mosaic virus, and the like. The promoter can be from a mammal or a mammalian pathogen such as CMV, SV40, RSV, MMV, HIV, and the like. In other examples the promoter can be from a fungus such as yeast (Gal 4 promoter), and the like, while in other examples it can be from bacteria or bacterial phage, for example lambda, T3, T7, SP6, and the like. The promoter can also be retroviral long terminal repeats (LTR), muscle creatine kinase promoter, actin promoter, elongation factor promoter, synthetic promoters, tissue-specific promoters and the like.

As used herein, the term "terminator" encompasses a DNA sequence represented at the end of the transcript that causes RNA polymerase to terminate transcription. Additionaly, the term "terminator" encompasses signal sequence that cause transcribed RNA to be processed before translation, for example, polyadenylation. This occurs at a discrete site downstream of the mature 3' end, which is generated by cleavage and polyadenylation. Any type of terminator can be used for these methods. For example, the terminator sequence can be derived from a prokaryotic or a eukaryotic, for example plant source. In one embodiment, artificial mammalian transcriptional terminator elements can be used. A nonexclusive list of terminator sequences include the SV40 transcription terminator, bovine growth hormone (BGH) terminator, synthetic terminators, rabbit beta-globin terminator, and the like. Terminators can also be a consecutive stretch of adenine nucleotides at the 3' end of a TAP fragment.

Tap Linker Molecules

As noted above, using TAP technology, genes can be amplified with additional elements such as promoter sequences, terminator sequences, binding sites for transcription factors, TATA box sequences, and enhancers. In addition, genes can be amplified with additional elements that can enable more rapid screening, characterization, purification and study of the polypeptides that they encode. These additional elements include for example, such as reporter genes, affinity tags, antibody tags, PNA binding sites, histidine tags, secretory signals, reporter genes and the like. One other such additional element that can be added to the TAP primary fragment or the TAP expression fragment are polynucleotides that encode linker molecules. The term "linker molecule" encompasses any molecule that is capable of immobilizing the polypeptides to a solid support.

In one embodiment, the linker molecule can be an epitope tag. In the modern molecular laboratory one is frequently faced with the task of detecting the expressed polypeptide in a variety of antibody-based experimental strategies, such as Western blot, immunoprecipitation, and immunocytochemistry with the use of fluorescently-tagged antibodies. To accomplish these various studies, availability of antibodies specific for each polypeptide would be most valuable. However, development of antibodies specific for all of the recombinant polypeptides being studied in a particular lab would be an expensive, time consuming and generally unrealistic proposition. This is a particularly daunting problem when one considers the rapidly expanding number of new genes with unknown function that are being revealed as a result of worldwide sequencing efforts.

Epitope tagging of TAP fragments is useful for rapidly and conveniently determining the intracellular distribution of the expressed product of TAP fragment, facilitating purification of polypeptides, identifying associated polypeptides, and characterizing new polypeptides by immunoprecipitation. Through the use of epitope tagging, recombinant polypeptides are expressed as fusion polypeptides bearing a short oligopeptide epitope added to the polypeptide coded by the natural gene of the target organism. Antibodies directed against the added epitope can then be used as tools for detection of the polypeptide in Western blot, immunocytochemistry, DNA band supershift experiments, fluorescence activated cell sorting (FACS) and affinity purification of the desired fusion polypeptides.

Accordingly, one embodiment of this invention is to modify the basic TAP system to create a fusion of the gene of interest and a polynucleotide sequence encoding a hemagglutinin (HA) epitope tag. The HA epitope tag is well characterized and highly immunoreactive. After transfection of this epitope tagged TAP fragment into cells, the resulting HA-tagged polypeptides can be identified with commercially available anti-HA antibodies. Accordingly, by amplifying a gene-of-interest with a HA epitope coding sequence, the expressed product can include the gene product and a HA epitope site. Accordingly, this expression product can be quickly captured and/or purified using antibodies specific for the HA epitope.

Likewise, a polynucleotide sequence encoding a histidine tag can be incorporated into the TAP fragment to enable the expressed gene product to be conveniently purified. The expression, purification, detection, and assay of recombinant polypeptides can be much more simple and powerful by the use of small affinity tags like the HA and the histidine tags. For example, the well-established QIAexpress Protein Expression and Purification Systems are based on the remarkable selectivity and affinity of patented nickel-nitrilotriacetic acid (Ni-NTA) metal-affinity chromatography matrices for polypeptides tagged with 6 consecutive histidine residues (6×His tag) available from QIAGEN (Seattle, Wash.).

The QIAexpress System is based on the remarkable selectivity of Ni-NTA (nickel-nitrilotriacetic acid) for polypeptides with an affinity tag of six consecutive histidine residues—the 6×His tag. This technology allows purification, detection, and assay of almost any 6×His-tagged polypeptide from any expression system. Polypeptides with a 6×His tag can be purified through nickel nitrilotriacetic (Ni-NTA) resin.

The TAP fragment can include tags designed to simplify detection and purification. One of the most powerful technologies for recombinant polypeptide purification is the addition of an affinity tag of six consecutive histidine residues. Polypeptides with a 6×His tag can be purified through nickel nitrilotriacetic (Ni-NTA) resin. The 6×His tag is much smaller than most other affinity tags and is uncharged at physiological pH. It rarely alters or contributes to polypeptide immunogenicity, rarely interferes with polypeptide structure or function, does not interfere with secretion, does not require removal by protease cleavage, and is compatible with denaturing buffer systems. Accordingly, this tag is a powerful tool for expression, assaying and purification of eukaryotic genes like protein kinases some of which are extremely difficult to clone using conventional plasmid-based cloning approach.

Oligonucleotides can be designed to include the nucleotide sequence encoding the 6×His epitope tag along with TAP promoter and terminator fragments from pCMVm and pTP-SV40, for example. For adding the 6×His epitope to the 5' end of the coding sequence, a sequencing encoding histidine residues can be included along with the promoter. For adding the 6×His epitope to the 3' end of the coding sequence, a sequencing encoding histidine residues can be included along with the terminator.

The HA and the 6×His epitope embodiments are not to be construed as limiting, and are provided for illustrative purposes. Those skilled in the art will appreciate that any type of linker molecule can be attached to the expressed products such as for example, a 7×, 8×, 9×, or 10× histidine tag, GST tag, fluorescent protein tag, Flag tag, and the like.

TAP Fragment with Secretory Signal

For many gene therapy and DNA vaccine applications it is beneficial for the gene product to be secreted from the transfected cells. For this reason a version of the TAP system and methods can be configured so that the gene product will contain a secretory signal. A commonly used signal peptide is the first 23 amino acids from human tissue plasminogen activator (tPA) with the coding sequence as follows: ATG GAT GCA ATG AAG AGA GGG CTC TGC TGT GTG CTG CTG CTG TGT GGA GCA GTC TTC GTT TCG CCC AGC. (SEQ ID NO: 1) This sequence can be built into the TAP promoter fragment to create a new TAP fragment in a fashion similar to the construction of the tagged polypeptides described above.

Incorporating TAP Fragments into a Plasmid Vector

Once the function or immunogenicity of a gene is identified by using TAP express, it can be of interest to clone it into a plasmid vector. TAP express is available from Gene Therapy Systems, San Diego, Calif. TAP cloning is a rapid and convenient way to accomplish this.

Once a gene with a specified function is identified through TAP Express, cloning it into a plasmid vector can be desirable to facilitate further gene characterization and manipulation. Standard cloning techniques can involve the use of restriction enzymes to digest the plasmid and the gene fragment to be inserted. Annealing and ligation of the compatible ends can lead to insertion of the gene into the vector. An alternative method of restriction ends-directed cloning is to prepare a linearized plasmid with T overhangs on the 3' ends of the double-stranded DNA to accommodate DNA fragments amplified with the aid of specific polymerases through PCR. This method is sometimes called "T/A cloning".

In certain embodiments, the TAP Cloning systems, methods, and kits can further simplify the cloning process by taking advantage of the universal 5' and 3' sequences that are present on the TAP Express fragment after the first or second PCR step. These regions overlap with the end sequences of our linearized TAP Express Cloning Vector. When the TAP fragment and the linearized plasmid are mixed together and directly electroporated into TAP Express Electro-Comp cells, endogenous bacterial recombinase activity recombines the two DNA fragments resulting in a plasmid with the inserted TAP Express fragment. This process can replace conventional cloning with two simple PCR steps. In some embodiments it does not require cutting, pasting and ligating DNA fragments. In addition, this process can be highly suited for fast and convenient cloning of TAP PCR fragments without having to resort to restriction enzymes, DNA ligase, Topo-isomerase or other DNA modifying enzymes. All "TAP" systems, vectors and cells are readily availabe from Gene Therapy Systems, San Diego, Calif.

GeneGrip PNA compatible TAP system can also be used to couple polypeptides onto DNA through PNA Dependent Gene Chemistry, which does not have the limitations of previously described methodologies. GeneGrip is available through Gene Therapy Systems, San Diego, Calif. This approach takes advantage of the property of peptide nucleic acids (PNA) to hybridize with duplex DNA in a sequence specific and very high affinity manner. PNA binding sites can be used for attaching a series of peptides onto DNA in order to target the transfected plasmid and improve transgene expression, for example. This can allow scientists to follow a rational approach to improve the efficiency and efficacy of gene delivery by adding elements intended to increase nuclear uptake, facilitate endosomal escape, or target gene delivery to the cell surface or to intracellular receptors.

Incorporating a GeneGrip site into TAP enables peptide nucleic acids (PNAs) to be hybridized to the TAP gene. Ligands can then be attached to the PNA in order to improve the bioavailability and DNA vaccine potency of the gene.

Automated System for Performing TAP Method

In another embodiment of the invention, a system can be used to perform every step involved in generating TAP fragments from a target organism. Additionally, each individual step is capable of being controlled by a system. For example, a system can design customized PCR primers, obtain said primers, perform PCR reactions utilizing TAP technology, attach promoters and terminators, and attach sequences that encode linker molecules to the primary or expression fragment. The system can be either automated or nonautomated.

Expression of the TAP Fragment

Transcriptionally active amplified DNA fragments can be directly used in various expression systems in order to obtain the corresponding polypeptide for each gene in the genome. The invention provides simple, efficient methods for generating transcriptionally active DNA fragments that can be readily transfected into animal cells or tissues by any nucleic acid transfection techniques. The methods can avoid the need for subcloning into expression vectors and for purification of plasmid DNA from bacteria. As skilled artisans can appreciate, TAP fragments can be rapidly expressed using in vivo or in vitro (e.g. cell-free) expression systems. For example, the amplified fragments can be directly transfected into a eukaryotic or prokaryotic cell for expression. Examples of eukaryotic cells that can be used for expression include mammalian, insect (e.g. Baculovirus expression systems), yeast (e.g. *Picchia pastoris*), and the like. An example of a prokaryotic cell expression system includes *E. coli*.

Alternatively, expression can be accomplished in cell free systems, for example, a T7 promoter system. Cell-free translation systems can include extracts from rabbit reticulocytes, wheat germ and *Escherichia coli*. These systems can be prepared as crude extracts containing the macromolecular components (70S or 80S ribosomes, tRNAs, aminoacyl-tRNA synthetases, initiation, elongation and termination factors, etc.) required for translation of exogenous RNA. To promote efficient translation, each extract can be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

The use of TAP technology allows skilled artisans to rapidly express a plurality of genes. After a particular gene of interest becomes transcriptionally active, other different genes can also be made to be transcriptionally active according to the methods of the invention. Accordingly, in one embodiment of the invention, a plurality of genes from a target organism are amplified and expressed in order to generate a library of polypeptides. In an embodiment of the invention, a library of polypeptides can be generated by expressing a plurality of TAP fragments. In another embodiment at least about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, or more different genes are expressed after becoming transcriptionally active through TAP technology.

Other embodiments of the invention relate to expressing the product of a polynucleotide that encodes a linker molecule. The polynucleotide encoding a linker molecule can be added to a TAP primary fragment or a TAP expression fragment. Accordingly, the linker molecule can be expressed with the gene of interest. As discussed above, in one embodiment, the linker molecule can be an epitope tag. An epitope tag is useful for facilitating purification of the expression product, identifying associated polypeptides, characterizing new polypeptides by immunoprecipitation, determining subcellular localization, and the like. One example of a particular linker molecule is the HA epitope tag. Accordingly, expression products containing a HA epitope can be quickly captured and/or purified using antibodies specific for the HA epitope. Other linker molecules include, for example, a 6×, 7×, 8×, 9×, or 10× histidine tag, GST tag, fluorescent protein tag, Flag tag, and the like.

The generation of polypeptide libraries according to the methods of the invention allows skilled artisans to easily use them in subsequent research and study. For example, it is possible to organize the expressed polypeptides into an array for further analysis. The expressed polypeptide arrays can be screened in order to identify new vaccine and drug targets against microbial, neplastic disease and the like, for example. The expressed polypeptides can be used to screen antibody libraries, to develop reagents, functional proteomic studies, and the like. All of these can be rapidly accomplished at rates far exceeding traditional methods.

Arrays made according to the methods of the invention may include about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266, about 300, about 350, about 400, about 450, about 500, about 550, about 600, about 650, about 700, about 750, about 800, about 850, about 900, about 950, about 1000, about 1050, about 1100, about 1150, about 1200, about 1250, about 1300, about 1350, about 1400, about 1450, about 1500, about 1600 about 1700, about 1800, about 1900, about 2000, about 2500, about 3000, about 3500, about 4000, about 4500, about 5000, about 6000, about 7000, about 8000, about 9000, about 10,000, about 15,000, about 20,000 about, 25,000, about 30,000 or more different polypeptides. Furthermore, this invention encompasses arrays where at least one of the polypeptides is attached to at least one linker molecule.

Human Proteome Through TAP

In one embodiment the complete human proteome, or a plurality of human polypeptides can be rapidly obtained and utilized to screen antibody libraries, for example. The complete human proteome can be generated in a very short time frame. The project can be divided into 4 steps. For example, the sequence of the human genome can be easily obtained by one of skill in the art from public genetic databases. Based upon the sequence information, approximately 27,000 transcriptionally active PCR (TAP) primary fragments encoding each gene in the human genome or a plurality of human genes can be generated. It should be noted that these approximately 27,000 fragments would not necessarily account for additional products produced by alternative splicing. The nucleotides coding sequences for these products can also be amplified and expressed.

The generation of approximately 27,000 fragments can require approximately 54,000 gene specific primers, which can be obtained rapidly generated by means and companies well known to those of skill in the art, Genset, for example. Once the primers are obtained the primary TAP fragments can be rapidly amplified using PCR machines. In certain embodiments the time can be greatly reduced by using machines capable of large numbers of reaction, for example, 768 reactions/machine.

The primary TAP fragments can then undergo subsequent PCR to generate approximately 27,000 transcriptionally active PCR (TAP) fragments. In one embodiment the TAP fragments can contain a T7 promoter, to be used in in vitro transcription/translation reactions. The TAP fragments can be generated and analyzed just as rapidly as the TAP primary fragments. The primers used to generate the TAP fragments are the same for all of the genes and they can be obtained and purchased in bulk quantities. The amount of each TAP Express fragment generated can be sufficient for at least 10, 15, 20, 100 or more transcription/translation reactions in 96-well plates. In alternative embodiments, the TAP fragments can conveniently be transferred into an expression vector using "TAP Cloning," as described for example in U.S. patent application Ser. No. 09/836,436 entitled "Fast and Enzymeless Cloning Nucleic Acid Fragments, which as noted above, is hereby incorporated by reference in its entirety. The cloned fragments can be saved and used for additional and future studies.

The approximately 27,000 TAP fragments can be used to synthesize the entire Human Proteome in a very short period of time. For example using a TAP fragment with a T7 promoter system, each TAP fragment can used in vitro with appropriate transcription/translation reagents in 96-well plates. In some embodiments using such a system, 10–50 micrograms of each protein can be generated, for example. The polypeptide preparations generated generally do not require further purification for use in antibody screening assays, for example. The proteome can be displayed on microchips and used to screen recombinant antibody libraries. The proteome can be used in cellular screening assays, for example. The antibodies can then be used, for example, to develop reagents. Alternatively, the antibodies can be used to ascertain polypeptide expression in various kinds of cells and tissue, such as for example, human tumor tissue to ascertain which polypeptides are expressed therein. This approach can be used to localize polypeptides in any tissue. The polypeptides can be screened for polypeptides involved in human disease, for example, such as immune diseases.

As mentioned above, TAP fragments can be generated by an automated system. In addition, polypeptides that are encoded by TAP fragments can be expressed using in vivo or in vitro (e.g. cell-free) expression systems. Expression products can be purified with the use of an automated system.

Adapter Technology

In addition to amplifying genes of interest using TAP technology, the present invention also encompasses amplifying genes using "adapter technology". In some embodiments adapter technology can utilize a one-step PCR reaction. The term "adapter technology" as used herein relates to methods of cloning a desired nucleic acid fragment into a vector by flanking a desired nucleic acid sequence, a gene of interest for example, with first and second adapter sequences. The resulting fragment can be contacted with the vector having sequences homologous to the first and second adapter sequences under conditions such that the nucleic acid fragment is incorporated into the vector by homologous recombination in vivo in a host cell. Accordingly, adapter technology allows for fast and enzymeless cloning of nucleic acid fragments into vectors and can also be used for forced cloning selection for successful transformation. Adapter technology is described in more detail in U.S. patent application Ser. No. 09/836,436, entitled "Fast and Enzymeless Cloning of Nucleic Acid Fragments", U.S. patent application Ser. No. 10/125,789, entitled "Rapid and Enzymeless Cloning of Nucleic Acid Fragments", and PCT Application No. PCTUS 02/123,34, all of which are hereby incorporated by reference in their entirety.

The nucleic acid fragment can be incorporated into any vector. In some embodiments, the vector that the fragment is incorporated into can be, for example, a plasmid, a cosmid, a bacterial artificial chromosome (BAC), and the like. The plasmid can be CoE1, PR100, R2, pACYC, and the like. The vector can also include a functional selection marker. The functional selection marker can be, for example, a resistance gene for kanamycin, ampicillin, blasticidin, carbonicillin, tetracycline, chloramphenicol, and the like. The vector further can include a dysfunctional selection marker that lacks a critical element, and wherein the critical element is supplied by said nucleic acid fragment upon successful homologous recombination. The dysfunctional selection marker can be, for example, kanamycin resistance gene, kanamycin resistance gene, ampicillin resistance gene, blasticidin resistance gene, carbonicillin resistance gene, tetracycline resistance gene, chloramphenicol resistance gene, and the like. Further, the dysfunctional selection marker can be, for example, a reporter gene, such as the lacZ gene, and the like.

The vector can include a negative selection element detrimental to host cell growth. The negative selection element can be disabled by said nucleic acid fragment upon successful homologous recombination. The negative selection element can be inducible. The negative selection element can be, for example, a mouse GATA-1 gene. The vector can include a dysfunctional selection marker and a negative selection element.

The vector can include a negative selection element detrimental to host cell growth. The negative selection element can be disabled by said nucleic acid fragment upon successful homologous recombination. The negative selection element can be inducible. The negative selection element can be, for example, a mouse GATA-1 gene. The vector can include a dysfunctional selection marker and a negative selection element.

The host cell used in adapter technology can be a bacterium. The bacterium can be capable of in vivo recombination. Examples of bacterium include JC8679, TB1, DHα, DH %, HB101, JM101, JM109, LE392, and the like. The plasmid can be maintained in the host cell under the selection condition selecting for the functional selection marker.

The first and second adapters can be any length sufficient to bind to the homologous sequences of the vector such that the desired nucleic acid sequence is incorporated into the vector. The first and second adapter sequences can be, for example, at least 11 bp, 12 bp, 13, bp, 14 bp, 15 bp, 16 bp, 17 bp, 18 bp, 19 bp, 20 bp, 21 bp, 22 bp, 23 bp, 24 bp, 25 bp, 26 bp, 27 bp, 28 bp, 29 bp, 30 bp, 31 bp, 32 bp, 33 bp, 34 bp, 35 bp, 36 bp, 37 bp, 38 bp, 40 bp, 50 bp, 60 bp and the like. Furthermore, the first and second adapter sequences can be greater than 60 bp.

The first and second adapter sequences further can include a functional element. The functional element can include a promoter, a terminator, a nucleic acid fragment encoding a selection marker gene, a nucleic acid encoding a linker molecule, a nucleic acid fragment encoding a known protein, a fusion tag, a nucleic acid fragment encoding a portion of a selection marker gene, a nucleic acid fragment encoding a growth promoting protein, a nucleic acid fragment encoding a transcription factor, a nucleic acid fragment encoding an autofluorescent protein (e.g. GFP), and the like.

When the common sequences on both the 5' and 3' ends of the nucleic acid fragment are complimentary with terminal sequences in a linearized empty vector, and the fragment and linearized vector are introduced, by electroporation, for example, together into a host cell, they recombine resulting in a new expression vector with the fragment directionally inserted. In alternative embodiments the host cell can include the linearized empty vector so that only the nucleic acid fragment is introduced into the host cell. It should be noted that in alternative embodiments of the present invention the vector can be circularized, and as used herein a vector can be either linearized or circular. The host cell is converted into an expression vector through homologous recombination. In principle this approach can be applied generally as an alternative to conventional cloning methods.

A nucleic acid fragment having first and second adapter sequences can be generated by methods well known to those of skill in the art. For example, a gene of interest with known 5' and 3' sequences undergoes PCR along with overlapping 5' and 3' priming oligonucleotides. The priming oligonucleotides can be obtained by methods known in the art, including manufacture by commercial suppliers. A primary fragment with adapter sequences can be generated. The adapter sequences flanking the gene of interest can be homologous to sequences on a vector or to sequences from other 5' or 3' fragments to be used in a subsequent PCR.

In some embodiments of the invention, a particular gene of interest from a target organism can be amplified with an adapter sequence on both the 3' and 5' ends. In other embodiments adapters can be attached to a plurality of genes, for example every gene, within a target organism's genome. In certain embodiments adapters can make the desired genes transcriptionally active. Once incorporated into the desired the vector, the desired gene can be rapidly replicated and expressed, such that a plurality of target organism's genes, for example every gene, is expressed.

Pluralities of expression products can be stored in libraries or arrays and can be assayed for their immunogenic properties as will be discussed below. While most embodiments relating to the assay methodologies are discussed in terms of TAP technology, all of the following assays can be used on adapter technology expression products as well. Once the appropriate assays are conducted on the adapter technology expression products, methods of developing vaccines can be utilized. While most of the embodiments relating to developing vaccines, discussed below, pertain to TAP technology, all of the vaccine embodiments can also be used with polypeptide libraries and arrays resulting from adapter technology.

Identifying Immunogenic Effect of Polypeptides

Libraries and arrays of polypeptides prepared through TAP or adapter technology and subsequent expression can be useful in the development of polypeptide or nucleic acid subunit vaccines. DNA vaccines are effective vaccines that are inexpensive to manufacture, and can be widely distributed. One of the most difficult tasks in developing a DNA vaccine (or any recombinant subunit vaccine) is the identification of the antigen that can stimulate the most effective immune response against the pathogen, particularly when the genome of the organism is large.

A comprehensive way to accomplish this is to obtain a plurality of polypeptides from a particular pathogen in the mode of a library or array. These polypeptides can be tested to determine their capability to evoke a humoral and/or a cell-mediated immune response. Polypeptides that evoke immunogenic responses can be tested individually or with other antigens for effectiveness as subunit vaccines. In addition, nucleic acids that code for identified antigenic polypeptides can also be used alone or with other nucleic acids that encode antigens to develop a subunit vaccine for a particular pathogen.

Although many of the embodiments described below relate to identifying the immunogenic effect of Vaccinia polypeptides, the methods of this invention can work with any target organism. In particular embodiments, the target organism can be a pathogen, such as, for example, Vaccinia virus, *B. anthracis, Clostridium botulism, Yersinia pestis, Variola major, Francisella tularensis*, Malaria, *Chlamydia trachomatis*, Streptococcus, *Borrelia burgdorferi, Helico-* bacter pylori, Mycobacterium tuberculosis, causative pathogens of viral hemorrhagic fevers, Ebola, Marburg, pox viruses, Arenaviruses, LCM, Junin virus, Machup virus, Guanarito virus, Bunyaviruses, Hantaviruses, Flaviruses, Dengue virus, Filoviruses, Coxiella burnetti, Brucella species, Burkholderia mallei, Ricinus communis, Clostridium perfringens, Staphylococcus, Rickettsia prowazekii and other Rickettsias, Food and Waterborne Pathogens, Diarrheagenic E.coli, Pathogenic Vibrios, Shigella species, Salmonella, Listeria monocytogenes, Campylobacter jejuni, Yersinia enterocolitica, Caliciviruses, Hepatitis A Protozoa, Cryptosporidium parvum, Cyclospora cayatanensis, Giardia lamblia, Entamoeba, histolytica, Toxoplasma, Microsporidia, Viral encephalitides, West Nile Virus, LaCrosse virus, VEE, EEE, WEE, Japanese Encephalitis Virus, Kysanur Forest Virus, Nipah virus, Tickborne hemorrhagic fever viruses, Crimean-Congo Hemorrhagic fever virus, Tickborne encephalitis viruses, Multi-drug resistant TB, Rabies virus, Rift Valley Fever virus, Lassa Fever virus, Influenza virus, and Yellow fever virus, and the like can be used in the present invention. This list of pathogens is provided only for exemplary purposes; skilled artisans can recognize numerous target organisms that can be used according to the methods of the present invention.

Vaccinia Virus Embodiment

Figure 2:
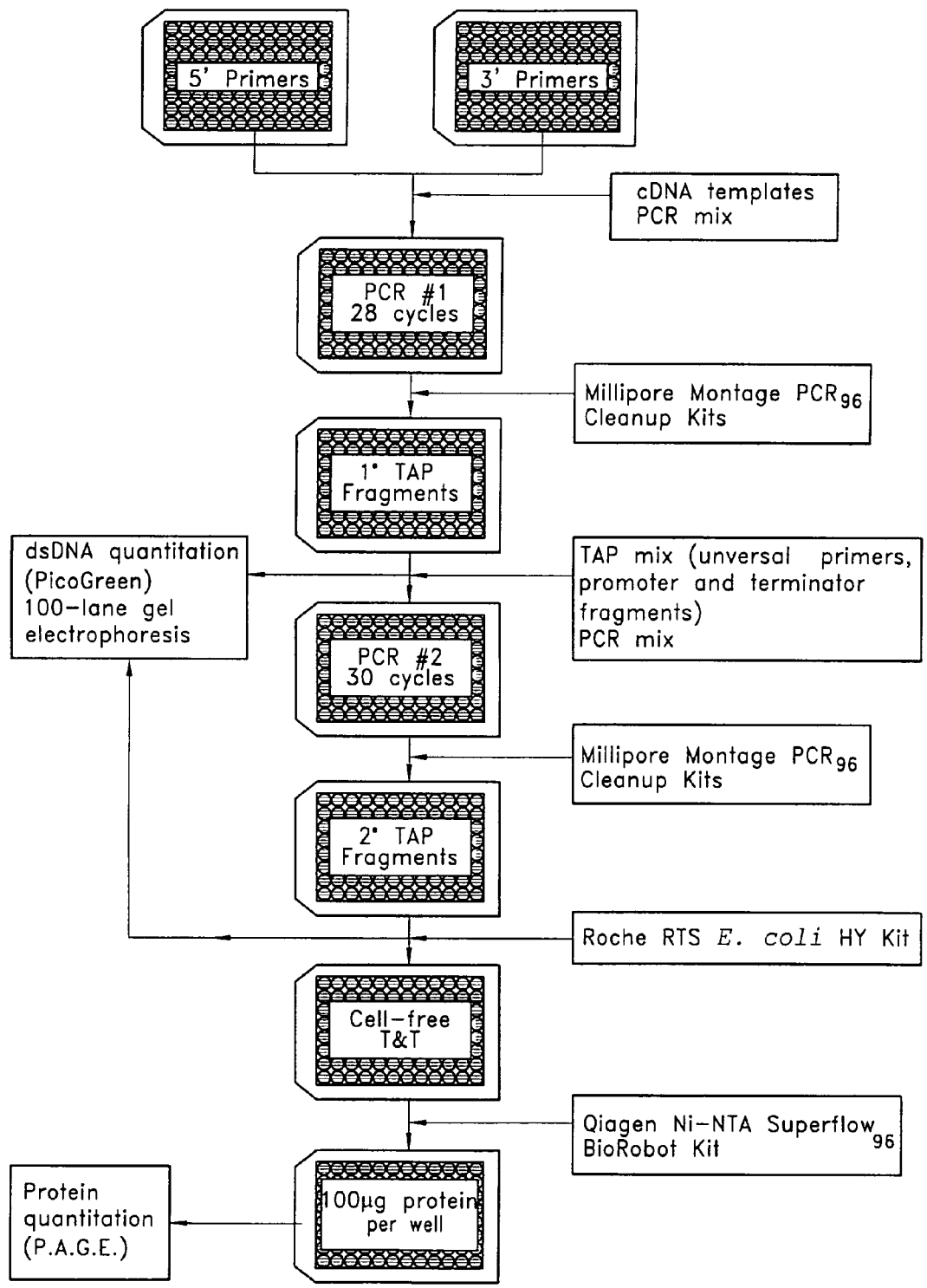
FIG. 2. displays a method of amplifying multiple genes using TAP technology, expressing said genes products, and purifying, and quantifying the resulting polypeptides.

One embodiment of the invention, incorporates a Rapid High-Throughput Vaccine Antigen Scanning approach, using TAP Express, that is able to systematically screen and identify all of the antigens in Vaccinia virus that give rise to a humoral and cell-mediated immune response. The identification of said Vaccinia antigens allows for the development of a highly specific subunit vaccine. FIG. 2 illustrates a method of amplifying multiple genes using TAP technology, expressing the gene products, and purifying, and quantifying the resulting polypeptides. FIG. 2 further illustrates a method of preparing polypeptides, which can be assayed to identify their ability to evoke a cell-mediated or humoral immune response.

In certain methods of developing a Smallpox vaccine, a plurality of Vaccinia genes can be made transcriptionally active. In one embodiment, the approximately 266 expression vectors encoding each of the 266 open reading frames from Vaccinia virus genome can be made transcriptionally active using TAP technology. The resulting TAP fragments can be purified and expressed in vitro or in vivo according to any method known in the art. The expression products, which encompass polypeptides, can be assayed to determine their ability to evoke a humoral and/or a cell-mediated immunogenic response. Polypeptides that are identified as capable of evoking an immune response can be used to develop polynucleotide or polypeptide subunit vaccines. The complete method will be described in more detail below.

According to one embodiment, gene specific PCR primers are designed in order to generate a plurality of transcriptionally active genes from the Vaccinia virus. In certain embodiments, primers are designed for every gene in the Vaccinia virus genome. In other embodiments, designing the primers allows a skilled artisan to make any given gene transcriptionally active using TAP technology.

As mentioned above, these PCR primers can be designed by using an automated system. For example, in order to design custom primers for use in the TAP process, a robotic workstation can be interfaced with a dual Pentium III CPU (1.4 GHz) computer running the Linux operating system. In addition, a customized MySQL database can manage all the input sequence data from GeneBank and from other sources. This database can track all the operations, samples and analytical data generated by the robot. In another embodiment, PCR primers, PCR products and polypeptides can be tracked by the database. For example, PCR primers, PCR products and polypeptides can be tracked by using bar coded 96-well plates. While the embodiments below discuss using 96-well plates in certain embodiments, those skilled in the art can appreciate that any sized well plate can be used. For example, the well plates can consist of about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 or more wells. In addition to well plates, the PCR products and polypeptides can be tracked using any suitable receptacles, for example test tubes.

Custom oligonucleotides, needed for the PCR reaction, can be generated or obtained in order to perform the TAP technology. In one embodiment, the Vaccinia virus genome sequence data and primer design software (Primer 3) can be used by the database to generate gene specific primers for all of the genes in the Vaccinia virus genome. The primers can be organized into arrays of about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 5' primers and 3' primers according to gene size and GC content, so that all of the optimal PCR reaction conditions can be the same for each plate. In addition, the gene specific primer sequences can be sent to an oligonucleotide synthesis provider (e.g., MWG Biotech, Inc, High Point, N.C.) where they can be synthesized. Synthesized primers can be organized and dispensed into bar-coded plates at a concentration of 100 pmole/µl, frozen and shipped to the practitioner. In one embodiment, 524 gene specific PCR primers, which are capable of amplifying each of the 266 Vaccinia virus genes are designed, generated, ordered, and organized.

After obtaining or generating the gene specific PCR primers, the genes can be amplified. In one embodiment, the primers can be organized into arrays of 96 5' primers and 96 3' primers according to gene size, and placed onto a robotic workstation. The robot can be programmed to generate a plate of about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 PCR reactions by mixing the appropriate 5' and 3' primers with Taq polymerase and Vaccinia virus genomic DNA. In addition, to Taq, any thermally stable polymerase can be used in the PCR reactions. For example, Vent, Pfu, Tfl, Tth, and Tgo polymerases can be used. The robotic workstation can transfer the PCR reaction plate containing the mixed reagents to a PCR machine for amplification. In one embodiment, the robotic workstation can use a robotic arm to transfer the PCR reaction plate to the PCR machine.

The first PCR procedure can be run for any number of cycles. In one embodiment, the PCR machine is run for about 20, 21, 22, 23, 24, 25, 26, 27, 28, 29, 30, 31, 32, 33, 34, 35, 36, 37, 38, 39, 40, or more cycles, for example. The first PCR reactions can be transferred robotically to a Millipore Montage 96-well cleanup kit, for example, when desired. Any method, kit or system can however, clean these reactions. According to one embodiment, a vacuum station of the robotic platform can carry out the purification step. In some embodiments, an aliquot of the resulting product can be transferred robotically to an analysis plate containing the Pico-Green fluorescent probe (Molecular Probes, Eugene, Oreg.) which reacts only with the dsDNA products. Depending on the number of wells, the plate can be transferred to an about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 or more well fluorescent plate reader. The fluorescent signal can be compared to a standard curve to determine the amount of double stranded PCR product generated in this first PCR step. Persons with skill in the art can adjust the above methods in order to optimize their particular PCR reaction, should the need arise.

In addition to the first PCR procedure, a second PCR reaction can be performed to add at least one sequence that confers transcriptional activity to the primary transcript. In one embodiment, the robot can be programmed to transfer an aliquot of each PCR reaction from the previous step into a PCR reaction containing a promoter and a terminator sequence. In a particular embodiment, the promoter can be a T7-histidine promoter fragment and the terminator can be a T7-histidine terminator fragment. Those with skill in the art can appreciate that any promoter or terminator sequence can be added to the primary transcript. In addition, any polynucleotide sequence that encodes a molecule allowing the expressed polypeptide to be detected or purified is also contemplated.

Like the first PCR reaction, the second PCR reaction can be run for any number of cycles. In one embodiment, the second PCR reaction is run for about 20, 21, 22, 23, 24, 25, 26, 27, 28, 29, 30, 31, 32, 33, 34, 35, 36, 37, 38, 39, 40 cycles or more. Furthermore, any type of thermally stable polymerase can be used for the second PCR reaction. In a particular embodiments the polymerase can be Taq. In some embodiments Vent, Pfu, Tfl, Tth, and Tgo polymerases can be used. The resulting PCR fragments from the second PCR reaction can be cleaned by any kit, method or system. A particular kit that can be used to clean the resulting TAP fragments is a Millipore Montage 96-well cleanup kit. Additionally, as discussed above, the level of PCR product recovered can be determined using any detection agent, for example, Pico-Green.

The resulting TAP fragments can be expressed by using any method of gene expression. In one embodiment, the TAP fragments can be expressed using in vivo or in vitro (e.g. cell-free) systems. For example, the fragments can be directly transfected into any eukaryotic or prokaryotic cell for expression. Examples of eukaryotic cells that can be used for expression include mammalian, insect, yeast, and the like. An example of a prokaryotic cell expression system includes *E. coli*. The TAP fragments can also be expressed by a cell free system. According to one embodiment of the invention, the resulting TAP fragments can be expressed in a high-throughput cell-free expression machine, such as, for example, the Roche RTS (Rapid Translation System) 100. In a further embodiment, the TAP fragments can be incubated in Roche RTS 100 system at 30° C. for 5 hours. A person with skill in the art can readily appreciate the utility in following the particular cell-free translation machine's instructions. If a T7-histidine promoter or terminator fragment is added to a primary transcript, translation of the TAP fragment can result in histidine tagged polypeptides, which can be purified as discussed below. As discussed herein, any tag can be used.

The Vaccinia polypeptides expressed can be purified using any purification method for purifying expressed polypeptides. In one embodiment histidine tagged polypeptides can be purified with Qiagen nickel columns, such as Ni-NTA Superflow 96 Biorobot Kit. A person with skill in the art can readily appreciate the utility in following the instructions of the particular polypeptide purification system. Other methods that can be used to purify polypeptides include ultrafiltration, extraction, and chromatography.

The identity, quantity and purity of the purified Vaccinia polypeptides can be verified by SDS gel electrophoresis. Under one embodiment, MALDI-TOF MS (Matrix Assisted Laser Desorption/Ionization-Time of Flight Mass Spectrometry) can be employed to confirm the fidelity of the purified polypeptides. According to this embodiment, aliquots of each polypeptide (1–2 µg) can be aliquoted into about 48, about 96, about 144, about 192, about 240, about 288, about 336, about 384, about 432, about 480, about 576, about 672, about 768, about 864, about 960, about 1056, about 1152, about 1248, about 1344, about 1440, about 1536 or more well plates and digested with modified trypsin. The resulting material can be mixed with matrix (alpha-cyano-4-hydroxy-cinnamic acid (CHCA)) and spotted onto any target plate with a suitable number of spots, for example, 48, about 96, about 144, about 192, about 240, about 288, about 336, about 384, about 432, about 480, about 576, about 672, about 768, about 864, about 960, about 1056, about 1152, about 1248, about 1344, about 1440, about 1536 or more spots. In one embodiment, a 384-spot "anchor chip" target plate (Bruker Daltonics, Billerica, Mass.) can be used. The plate can be transferred to the sample stage of a Bruker Autoflex MALDI-TOF mass spectrometer. The spectrometer can be set up to automatically scan the plate and search the Mascot polypeptide database via the Internet. Accordingly, a very rapid verification system can verify purity, identity, and quantity in less than a day, for example, depending on the amount of polypeptides. Purified polypeptides can be placed in libraries or organized into arrays for subsequent testing and analysis.

Humoral Immune Response

Use of the Vaccinia virus polypeptide libraries and arrays prepared, for example, according the methods above (e.g. using TAP or adapter technology) can be used to identify antigenic targets of humoral immunity in Vaccinia vaccinated animals. A humoral immune response relates to the generation of antibodies and their ability to bind to a particular antigen. In general, the humoral immune system uses white blood cells, which have the ability to recognize antigens, to generate antibodies that are capable of binding to the antigens.

In one embodiment, the Vaccinia polypeptides are generated according to the methods described above. In a more particular embodiment additional polynucleotide sequences that encode linker molecules are added to the TAP primary fragment or the TAP expression fragment such that the expressed product can include the gene product attached to a linker molecule. As discussed previously, the term "linker molecule" encompasses molecules that are capable of immobilizing the polypeptides to a solid support.

In a particular embodiment, a Vaccinia gene-of-interest is combined with a HA epitope coding sequence such that the expressed product can include the Vaccinia gene product and a HA epitope site. In another embodiment, a Vaccinia gene of interest is combined with a histidine coding sequence, such that the expressed product can include the Vaccinia gene product and a 6×, 7×, 8×, 9×, or 10× histidine tag. In other embodiments a Vaccinia gene is combined with a sequence that codes for a GST tag, fluorescent protein tag, or Flag tag. Using these methods it is possible to express and tag every Vaccinia virus polypeptide encoded by its genome. In another embodiment, the tagged Vaccinia virus polypeptide can be attached to a solid support, such as a 96-well plate. The attached polypeptides can come into contact with serum or other fluid containing B lymphocytes from an animal that has been immunized with one or more antigens from a Vaccinia virus. In one embodiment, a typical ELISA assay can be performed to detect the presence of antigen specific antibodies.

As an example of an ELISA assay, tagged Vaccinia polypeptides can be bound to a solid support, such as a 96-well plate. The bound Vaccinia polypeptides can be incubated with serum from an animal that has been immunized with one or more antigens from a Vaccinia virus. The reaction mixture can be washed to remove any unbound serum antibodies. The ability of the serum antibodies to bind to the bound Vaccinia polypeptides can be detected using numerous methods. For example, enzyme linked secondary antibodies can be added to detect the presence of an antigen specific antibody. Any enzyme linked secondary antibody can be used in this invention, depending on the source of the serum. For example, if vaccinated mouse serum is used to provide the primary antibody, enzyme linked anti-mouse antibody can be used as a secondary antibody. Likewise if human serum is used to provide the primary antibody, enzyme linked anti-human serum can be used as a secondary enzyme.

Any suitable assay can be used to determine the amount of bound polypeptide specific antibody. Also, skilled artisans can develop the enzyme assay to determine the amount of polypeptide specific antibody that is bound. In one embodiment, the readout from an assay can show the presence of different levels of antibody in each of the 96 wells. For example, while some Vaccinia virus polypeptides can not generate any serum antibodies, other polypeptides can generate intermediate levels of antibodies, and some can generate high antibody levels. In one embodiment, polypeptides that generate high antibody titers can be further researched to determine which polypeptides are present on the surface of the virus. In a particular embodiment, polypeptides that generate high antibody titers and that are located on the surface of the virus can be good candidates for use in the development of a subunit Smallpox vaccine.

Figure 3:
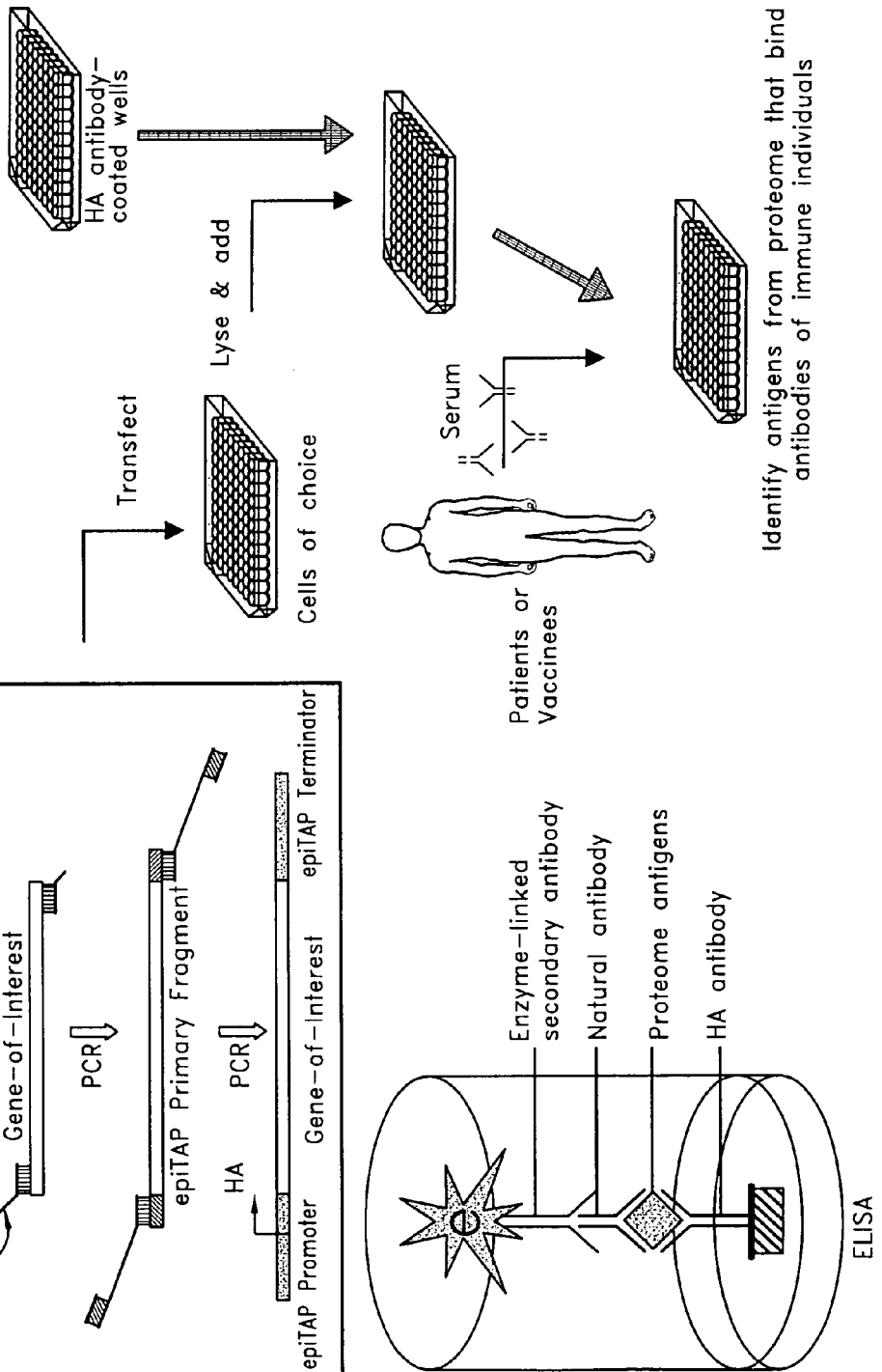
FIG. 3. demonstrates how a plurality of polypeptides from a target organism can be assayed to determine each polypeptide's ability to elicit a humoral immune response.
Figure 4:
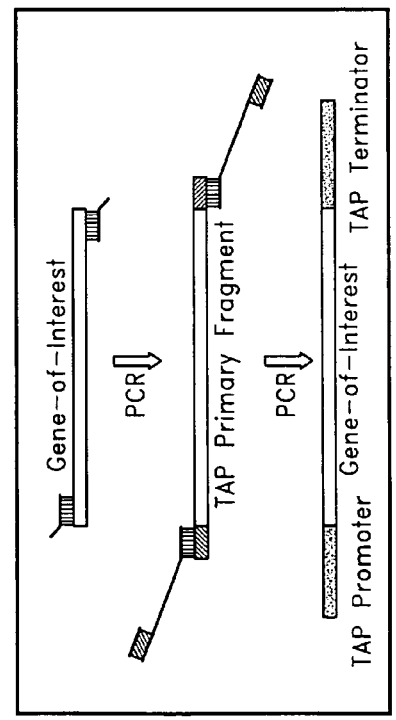
FIG. 4. demonstrates how a plurality of polypeptides from a target organism can be assayed to determine each polypeptide's ability to elicit a cell mediated response.
Figure 4:
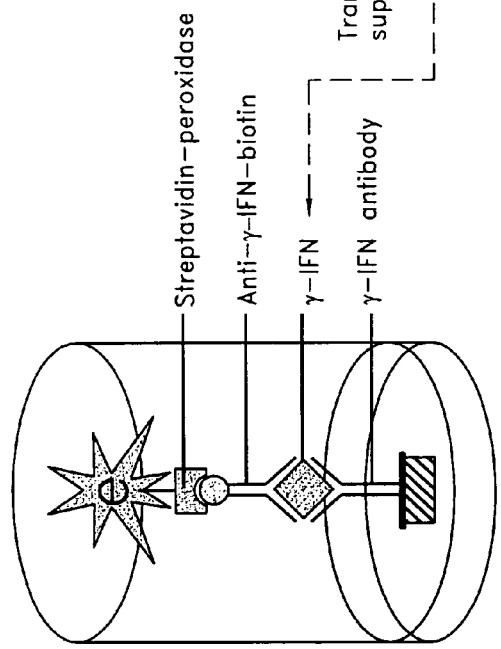

FIG. 3 demonstrates one embodiment of determining the humoral immune response generated by an array of polypeptides. One of skill in the art may deviate in certain details from those shown in FIG. 3. For example, the HA tag may be placed at either the C-terminal or N-terminal end of the polypeptide to insure that epitopes are not concealed due to binding to the plate. Instead of HA tagged polypeptides, a histidine tag can be used, and the polypeptides can be bound to nickel coated plates. For example a 6×, 7×, 8×, 9×, or 10× histidine tag can be used. Alternatively, histidine tagged polypeptides can be purified from either transfected cells or from the in vitro transcription translation system. Purified polypeptides can be attached non-specifically to polypeptide absorbing plates such as Immulon plates, for example.

Cell-Mediated Immune Response

Use of the Vaccinia virus polypeptide libraries and arrays prepared according the methods above (e.g. using TAP or adapter technology) can also be used to identify the antigenic targets of cell-mediated immunity in Vaccinia vaccinated animals. In contrast to a humoral immune response, where an antibody binds directly binding to an antigen, a cell-mediated immune response relates to T-cells binding to the surface of other cells that display the antigen. When certain T-cells come into contact with a presented antigen, they produce and release cytokines such as interferon-γ (TNF-γ) or Tumor Necrosis Factor-alpha (TNF-α). Cytokines are cellular signals that can alter the behavior or properties of another cell. For example, cytokines may inhibit viral replication, induce increased expression of MHC class I and peptide transporter molecules in infected cells, or activate macrophages. Accordingly, cytokines released by T-cells, associated with the binding to an antigen, can be used to identify and detect T-cell/antigen interactions.

Some cells have MHC molecules on their membranes to present antigens to T-cells. Efficient T-cell function relies on proper recognition of the MHC-antigen complex. There are two types of MHC molecules: Class I and Class II. The two different classes of MHC molecules bind peptides from different sources inside the cell for presentation at the cell surface to different classes of T-cells. Any T-cell can be used in the present invention, and include for example both $CD4^+$ and $CD8^+$ T-cells. $CD8^+$ cells (cytotoxic T-cells) bind epitopes that are part of class I MHC molecules. $CD4^+$ T-Cells, which includes inflammatory CD4 T-cells and helper CD4 T-cells, bind epitopes that are part of class II MHC molecules. Only specialized antigen-presenting cells express class II molecules.

There are three main types of antigen-presenting cells: B cells, macrophages and dendritic cells. Each of these cell types is specialized to process and present antigens from different sources to T-cells, and two of them, the macrophages and the B cells, are also the targets of subsequent actions of armed effector T-cells. These three cell types can express the specialized co-stimulatory molecules that enable them to activate naive T-cells, although macrophages and B cells express those molecules only when suitably activated by infection.

Embodiments of the present invention relate to detecting Vaccinia polypeptides capable of evoking a cell-mediated immune response in order to identify potential candidates for use in a subunit vaccine or other pharmaceutical composition. According to one method of detecting a cell-mediated immune response, a polypeptide is delivered into an antigen-presenting cell where it can be presented in a manner that is recognized by antigen specific T-cells. In another embodiment of the invention, a transcriptionally active gene can be delivered into an antigen-presenting cell where expressed and presented in a manner that can be recognized by an antigen specific T-cells. Antigen specific T-cells can be acquired from numerous sources. For example, animals that have been immunized with one or more antigens from Vaccinia virus are a good source of antigen specific T-cells. For example, a human volunteer immunized with Vaccinia can be a source of antigen specific T-cells.

In order to test the ability of Vaccinia polypeptides to elicit a cell mediated response, a plurality of Vaccinia genes can be amplified and made transcriptionally active using TAP technology. In one embodiment about 10, about 20, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 266 Vaccinia virus genes are made transcriptionally active using TAP technology.

Transcriptionally active genes can be transfected into an antigen-presenting cell and expressed within the cell. In another embodiment, instead of transfecting the genes into an antigen-presenting cell, the genes can be expressed in an in vivo or in vitro (cell-free) expression system and the expressed polypeptide can be delivered into the antigen-presenting cell. The polypeptide can be delivered into the antigen-presenting cell according to any method. In one embodiment, the polypeptide can be delivered using the technology described in U.S. patent application Ser. No. 09/738,046, entitled "Intracellular Protein Delivery Reagent" and U.S. patent application Ser. No. 10/141,535, entitled "Intracellular Protein Delivery Compositions and Methods of Use," both of which are hereby incorporated by reference in their entirety. The reagents described therein are is capable of delivering any type of polypeptide into any type of cell. Furthermore, the results of FIG. 5 demonstrate that dendritic cells can present antigens to T-Cells supplied from an immunized host after antigenic polypeptides were delivered to the dendritic cells with reagents from the above mentioned applications.

In certain embodiments, reagents used to deliver polypeptides into cultured cells can be a cationic lipid formulation. In one embodiment, these reagents can deliver fluorescently labeled antibodies, high and low molecular weight dextrans, phycoerythrin-BSA, caspase 3, caspase 8, granzyme B, and β-galactosidase into the cytoplasm of a variety of different adherent and suspension cells. Caspases delivered to cells with are functional, since they can be shown to send cells into apoptosis. In one embodiment, Vaccinia polypeptides are delivered into dendritic cells using these reagents.

Detecting a T-cell's ability to bind to an antigen-presenting cell, after the antigen-presenting cell has processed a particular polypeptide, is useful in determining whether the particular polypeptide evokes a cell-mediated immune response. Once a particular polypeptide is delivered into or expressed in the antigen-presenting cell, an assay can be performed to identify T-cell interaction with the MHC-antigen complex. In one embodiment, it can be determined if T-cells obtained from an animal that was immunized with Vaccinia can bind to a particular antigen presented by an antigen-presenting cell. For example, an EliSpot assay can be performed to identify antigen specific T-cells. Similar immunoassays can be performed to identify Vaccinia antigens (presented by an antigen-presenting cells) that stimulate T-cells from Vaccinia immunized individuals.

One method of detecting a T-cell/antigen interaction is to measure the amount of a particular cytokine released by the T-cell when it interacts with a MHC-antigen complex. The skilled artisan can appreciate that other cellular signals can be used to indicate a cell-mediated immune response. In one embodiment, the levels of IFN-γ released by T-cells can indicate whether a particular peptide is capable of evoking a cell-mediated immune response. In a particular embodiment, an antibody specific for IFN-γ can be coated onto a solid support. Unbound antibodies can be washed away and IFN-γ obtained from the supernatant containing T-cells plus antigen-presenting cells or antigen transduced antigen-presenting cells, can be added to the wells. A biotinylated secondary antibody specific for IFN-γ can be added. Excess secondary antibody can be removed and Streptavidin-Peroxidase can be added to the mixture. Streptavidin-Peroxidase is capable of binding to the biotinylated antibody to complete the four-member immunoassay "sandwich." Excess or unbound Streptavidin-Peroxidase is easily removed from the mixture. In order to detect amount of bound Sterptavidin-Peroxidase, a substrate solution can be added which reacts with the Streptavidin-Peroxidase to produce color. The intensity of the colored product is directly proportional to the concentration of IFN-γ present in the T-cell/antigen-presenting cell supernatant. Kits for performing these types of immunoassay are readily available from many commercial suppliers or the necessary reagents composing such kits can be purchased separately or produced in-house. In one embodiment, processed and presented Vaccinia polypeptide that evokes T-cells to produce a high level of IFN-γ can be considered a strong candidate for use in developing a subunit vaccine.

Those with skill in the art will appreciate that other methods can be used to detect T-cell/Antigen interactions. These methods include bead based assays, flow-based assays, RT-PCR based assays, cytokine ELISAs, lymphoproliferation assays, cytotoxic T cell assays, or any other assay that can detect the interaction of a T-cell with a responder cell (e.g. macrophage).

*Plasmodium falciparum* Embodiment

As like the Vaccinia embodiment, the methods and apparatus disclosed in the following *Plasmodium falciparum* embodiment are applicable to any given target organism or cell. Accordingly, this embodiment is not provided as a limitation on the present invention, but rather as a working example of a particular target organism.

Malaria is the most important parasitic disease of man. Its resistance to chemoprophylactic and chemotherapeutic agents is increasing, and the development of an efficacious Malaria vaccine is recognized as an international public health priority. Progress toward development of a Malaria vaccine has been hindered in part by the complex life cycle of the parasite. The parasite develops in numerous intracellular and extracellular environments and it has a large 26 megabase genome that contains over 5000 genes. Many of these genes are expressed in different stages of the life cycle and they vary extensively between strains.

The genome of *Plasmodium falciparum*, the parasite responsible for Malaria, is predicted to encode more than 5,000 polypeptides, each of which is a potential antigen useful for a DNA or polypeptide vaccine. The time and expense of expressing and screening every *Plasmodium falciparum* polypeptide is greatly reduced using the methods of the current invention. It is now possible to identify the most efficacious antigens for a DNA or polypeptide vaccine, as well as provide the foundation for establishing stage specific expression and subcellular localization and functional activity of these antigens.

Two types of immunization have been found to be effective for achieving protection against Malaria infection in animals and humans. Immunization with either the whole parasite, or with radiation-attenuated sporozoites induces immunity at the pre-erythrocytic stage. Naturally acquired immunity to Malaria develops against the erythrocytic stage. These observations offer confidence that the development of a Malaria vaccine may be feasible, however, the current generation of subunit vaccines provide neither optimal protection nor protection on genetically diverse backgrounds.

The systems, methods, kits and arrays of the present invention can be used to systematically assay to quantify the humoral and cellular immune responses against each individual antigen in the Malaria genome from people exposed to Malaria. This information can be used to identify new target antigens for the next generation of Malaria DNA vaccines.

Therefore, the systems, methods, kits and polypeptide arrays can be used as an alternative approach for the development of an effective Malaria vaccine based on the presumption that duplicating the protection induced by whole organism vaccination may require a vaccine as complex as the whole organism itself. A new vaccine according to this invention incorporates a sufficient number of antigenic epitopes and induces an appropriate immune response in the context of diverse host genetics. This entails the identification of an unprecedented number of parasite-derived polypeptide antigens and the development of vaccine delivery system(s) based on those antigens, in order to reproduce the breadth and multiplicity of the whole organism induced protective immunity. Accordingly, the present invention can capitalize on the genomic sequence data derived from the Malaria genome project to identify antigenic targets expressed in the two different routes of effective immunization.

The methods, systems, and kits described herein can be used to generate transcriptionally active PCR (TAP) fragments from any gene of interest in 2 sequential PCR reactions. TAP fragments can be transfected into cultured cells or injected into animals resulting in expression levels comparable to supercoiled plasmids encoding the same polypeptides. Moreover, when TAP fragments encoding immunogenic antigens are injected into animals, antibody titers comparable to those induced by supercoiled plasmids are generated.

Human volunteers immunized with irradiated sporozoites develop a repertoire of humoral and cellular immune responses against hundreds or thousands of antigens expressed by the Malaria parasite within the host hepatocyte. The resulting immune responses, directed primarily against liver stage antigens, are sufficient to protect immunized individuals from a subsequent challenge with infectious *P. falciparum* sporozoites. On the other hand, the protection induced in individuals by natural exposure to Malaria is mediated primarily by antibodies directed against parasite polypeptides expressed during the erythrocytic stage of the parasite's life cycle. A third relevant group of individuals is a subgroup of those that are naturally exposed to Malaria that are chronically parasitemic but clinically asymptomatic. For reasons that are unclear, these patients are typically asymptomatic although they may periodically develop clinical symptoms. Fluctuations in the immune response to certain antigens may account for this cycle of remission and clinical disease.

The central assumption, based on the two human models of whole organism induced immunity against Malaria (the irradiated sporozoite model and the naturally acquired immunity model), is that of the over 5,000 Malaria antigens there will be one subset that is the target of protective T cell responses directed against the polypeptides expressed by the liver stage organism and another subset that is the target of protective antibodies directed against polypeptides expressed during the erythrocytic stage. A goal of this invention is to develop a rapid, high throughput approach to identify and catalog all of the Malaria polypeptides responsible for generating protective cellular and humoral immune responses in man, and to compare the responses induced by irradiated sporozoite immunization with the responses induced by natural exposure to Malaria.

This rapid vaccine antigen scanning system can be used to characterize the immune responses in different populations of Malaria-exposed individuals including those with mild disease, severe disease, cerebral Malaria, maternal infections (pregnancy), and asymptomatic parasitemia. Since clinical disease and acquired immunity are also influenced by the age of the individual, the immune responses in infants, children and adults can be monitored. The immune responses in clinically symptomatic and asymptomatic patients will be compared to identify immune responses against specific antigens that that are capable of keeping the clinical disease in check. These antigens will be particularly appropriate candidates for prophylactic vaccine development and can also be useful in the context of a therapeutic vaccine to treat the asymptomatic parasitemic population to reduce the frequency of clinically symptomatic episodes.

Figure 6:
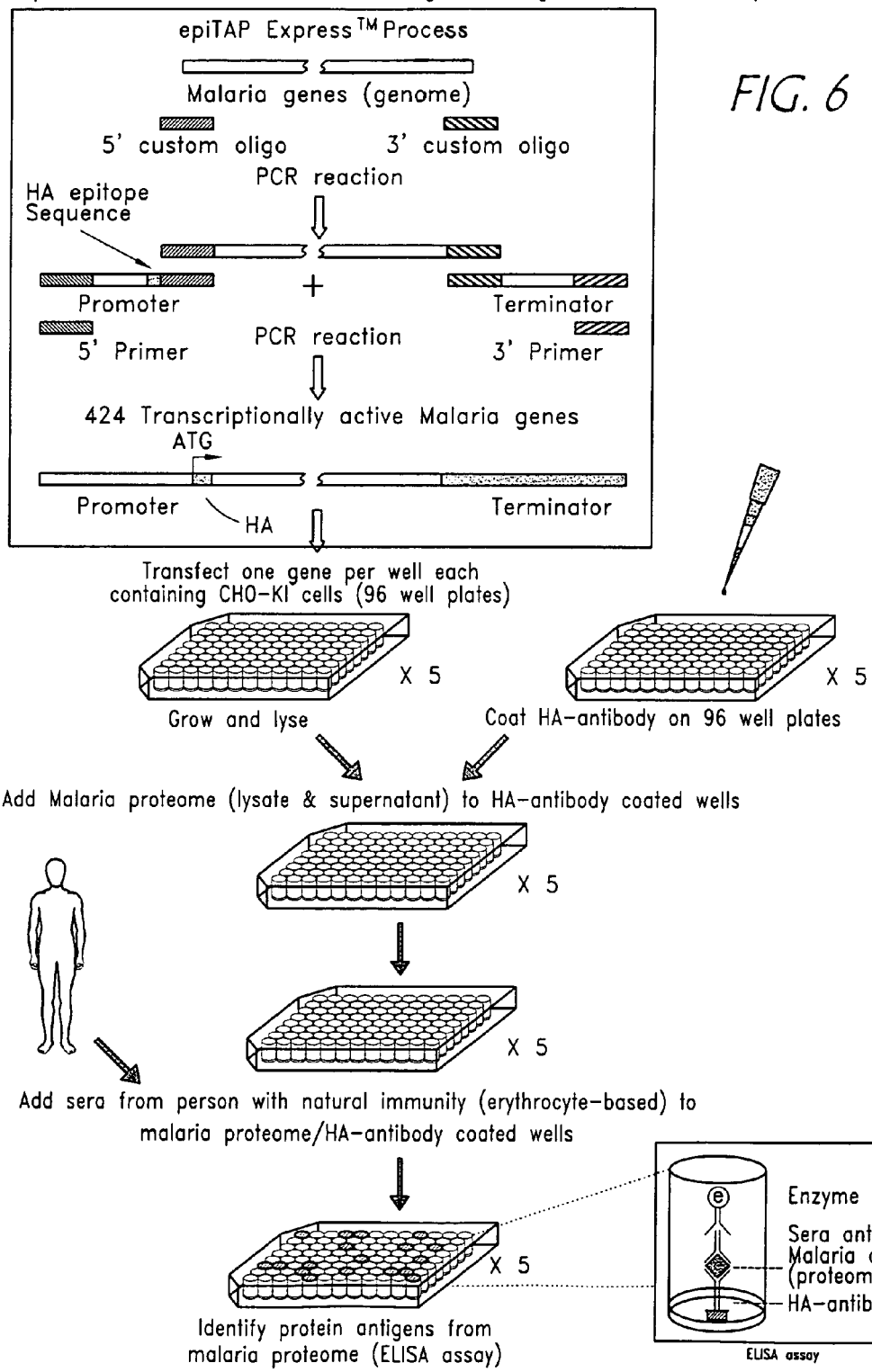
FIG. 6. illustrates a humoral vaccine antigen scan. HA-EpiTAP fragments encoding 424 different antigens from *P. falciparum* can be amplified and individually transfected into separate well of 596-well plates containing UM449 cells. The cells are lysed and the supernatants and lysates are transferred to another set of 96-well plates containing HA antibody bound to the surface of the plates. The HA antibody can capture the HA epitope tagged antibody that is present in the cell lysate. Serum from an infected individual is added to each well and the antigen in the bottom of the well can capture the anti-malaria antibody present in the serum. The bound anti-malaria antigen antibody are quantified by using an anti-human detecting antibody. Naturally immunized individuals generally may display those antigens against the blood stage organism, whereas sporozoite immunized individual generally have antibodies against the hepatic stage organism.
Figure 7:
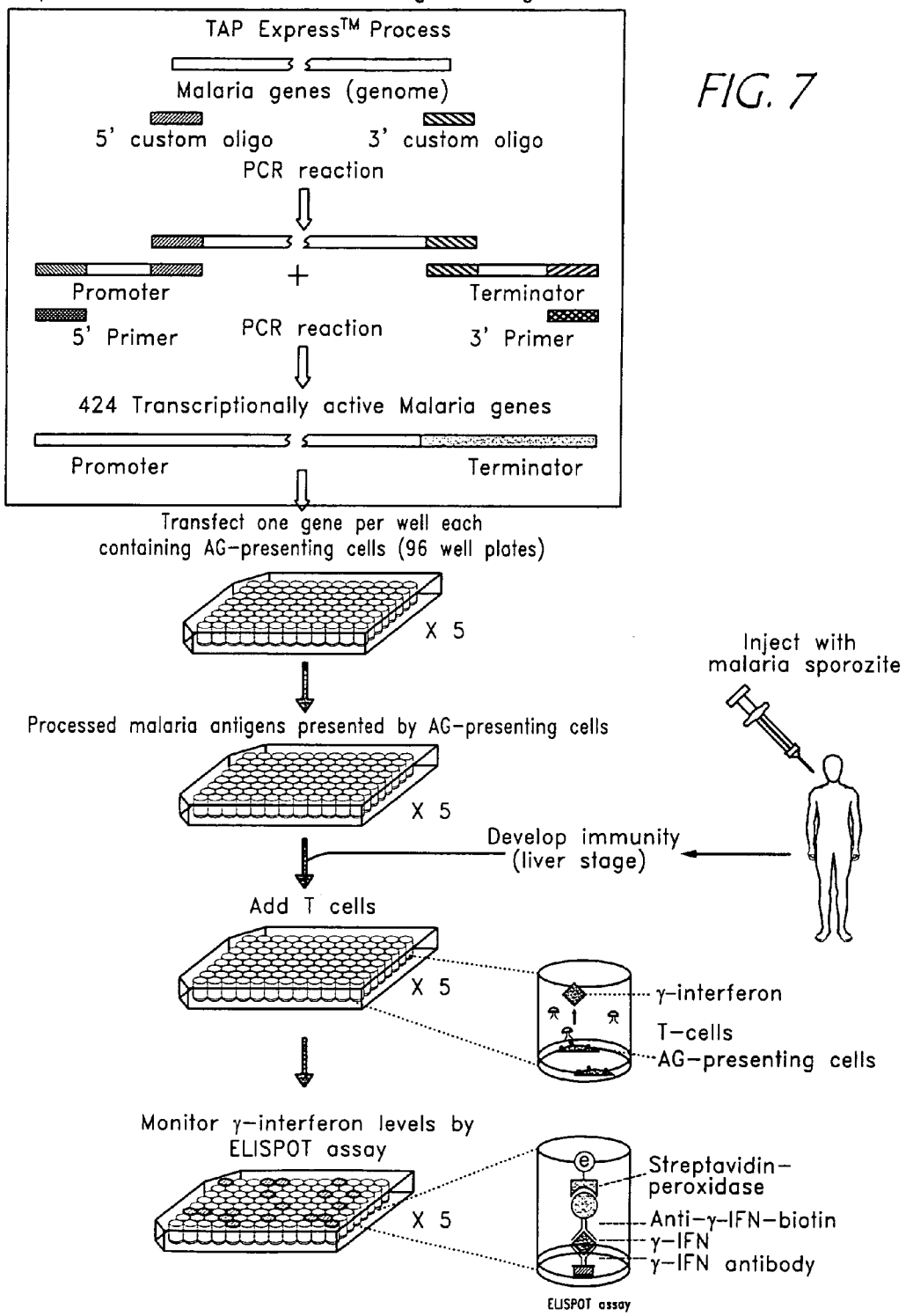
FIG. 7. illustrates a cellular vaccine antigen scan. TAP fragments encoding 424 different antigens from *P. falciparum* are amplified and individually transfected into haplotype matched antigen presenting cells in 96-well plates. T-cells isolated from the blood of immunized individuals are mixed with the transfected cells and interferon gamma production is monitored by Elispot assay. A larger number of potential antigens contributing to the protective response in sporozoite individuals are discovered by this approach.
Figure 8:
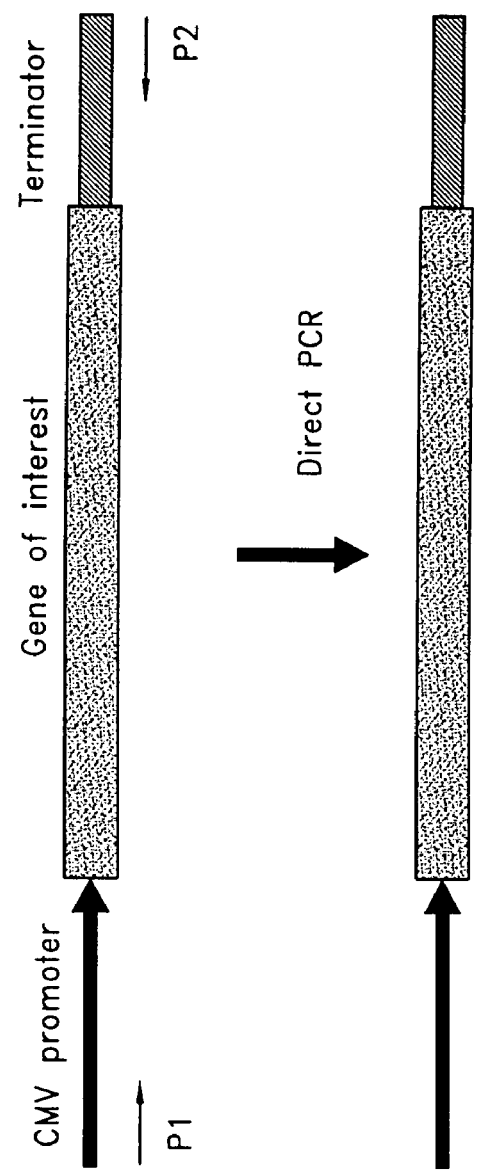
FIG. 8. illustrates a PCR amplification product generated from a CMV based plasmid template using 5' and 3' primers (P1 and P2) that flank the promoter and terminator. This produces a PCR fragment that encodes the reporter gene flanked by full length promoter and terminator sequences.
Figure 9:
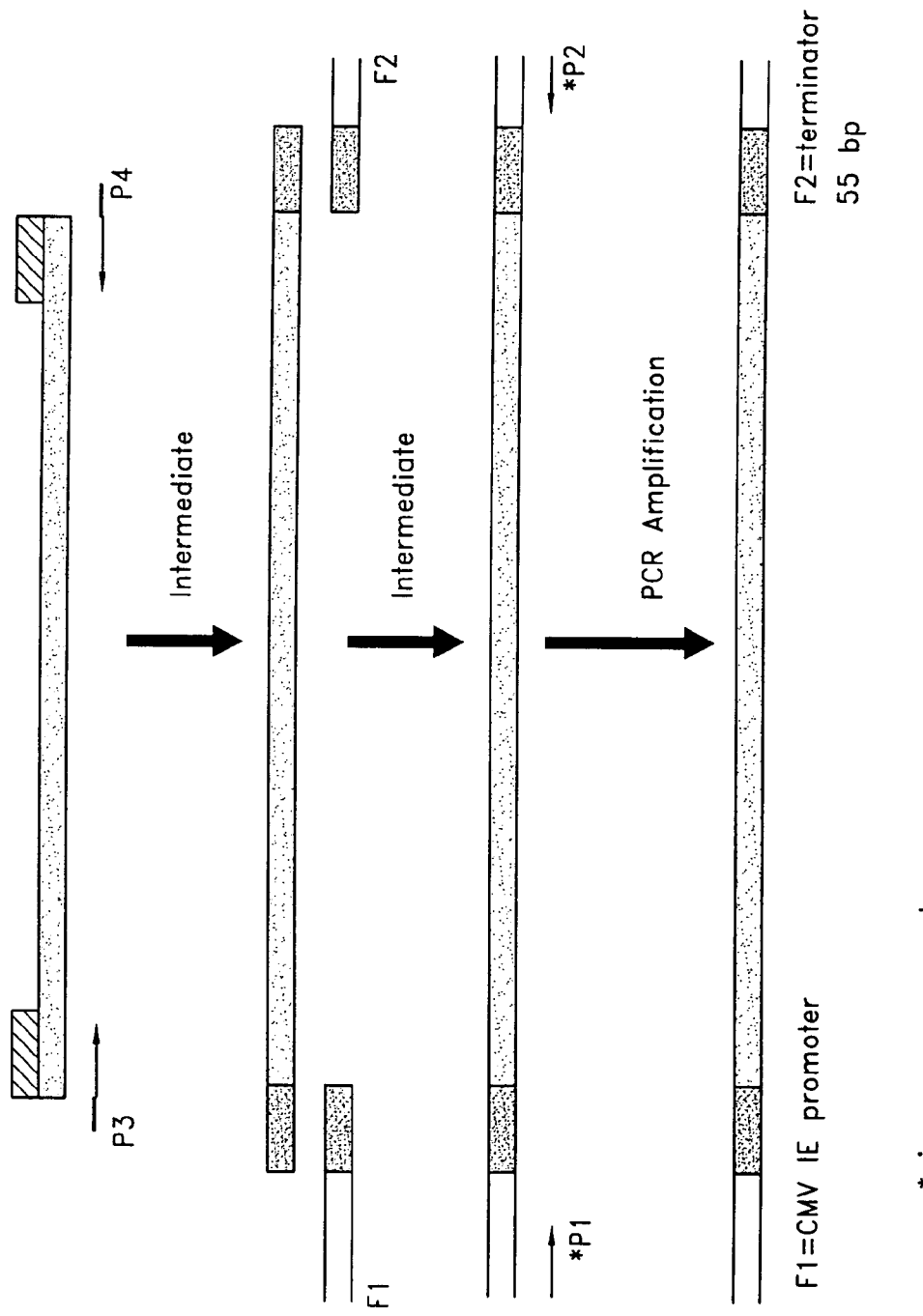
FIG. 9. illustrates catalytic amounts of promoter and terminator fragments (F1 and F2) mixed with catalytic amounts of gene specific primers (P3 and P4). Primers P3 and P4 also have a ~20 nucleotide sequence complementary to the promoter and terminator. Excess amounts of primers P1 and P2 which complementary to the 5' and 3' ends of the promoter and terminator are used to amplify the product leading to a gene fragment with flanking promoter and terminator sequences.
Figure 10:
FIG. 10. illustrates plasmids that can be used as the source for the TAP terminator and TAP promoter fragments.
Figure 11:
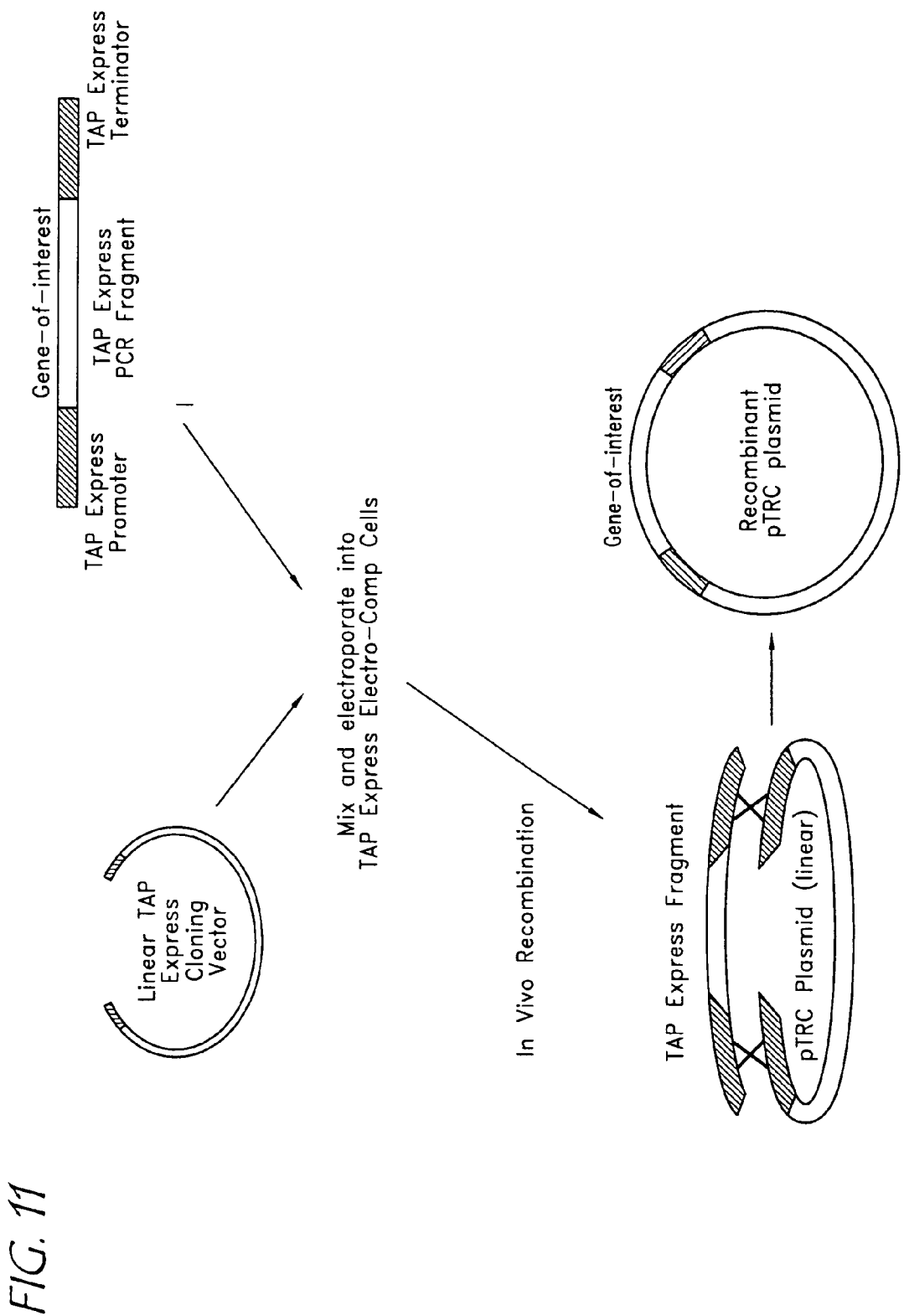
FIG. 11. illustrates the TAP Cloning Scheme. TAP fragments can be mixed with a linearized plasmid containing complementary ends and the mixture can be electroporated into host bacterial cells containing high recombinase activity. Most of the resulting stable colonies contain plasmid with the gene of interest directionally inserted.

The rapid vaccine antigen scanning approach of the present invention is illustrated in FIGS. 6 & 7. As mentioned earlier, these approaches can be applied to any type of organism or cell. Illustrated is an approach for scanning the Malaria genome, as an example. An exemplary procedure is detailed below. For the Humoral Antigen Scan (FIG. 6), HA-Epitope TAP fragments encoding each of the Malaria antigens are individually amplified. One microgram of each fragment is mixed with two micrograms of the transfection reagent, such as the GenePORTER reagent (Gene Therapy Systems, San Diego, Calif.) and the mixture is transferred to 96-well plates containing CHO-K1 or UM449 cells. The transfection continues for 48 hours, the cells are lysed, and the supernatant and lysate are transferred to another set of 96-well plates that are coated with anti-HA antibody. Since each of the HA-EpiTAP fragments contain the HA epitope, some of the HA epitope tagged polypeptide in the lysate bind to the HA antibody coated plates.

In another embodiment, the cells are not lysed in order to capture the expression product. More specifically, where the expression product is either secreted from the cell and/or is expressed on the cell surface, the cells themselves as opposed to their lysate can be used to capture the expression product using an appropriate assay. In this embodiment, where no lysing takes place, the capture assay can take place in the same plate or plates that the transfection took place in.

In addition to using cell systems, those with skill in the art can obtain TAP expression products using cell-free transcription and translation systems, for example, a T7 promoter system. Cell-free translation systems can include extracts from rabbit reticulocytes, wheat germ and *Escherichia coli*. These systems can be prepared as crude extracts containing the macromolecular components (70S or 80S ribosomes, tRNAs, aminoacyl-tRNA synthetases, initiation, elongation and termination factors, etc.) required for translation of exogenous RNA. To promote efficient translation, each extract can be supplemented with amino acids, energy sources (ATP, GTP), energy regenerating systems (creatine phosphate and creatine phosphokinase for eukaryotic systems, and phosphoenol pyruvate and pyruvate kinase for the *E. coli* lysate), and other co-factors ($Mg^{2+}$, $K^+$, etc.).

In order to ensure that certain Malaria epitopes are not masked by binding of the polypeptide to HA antibody, two versions of the HA-epitope tag approach can be used; one version has the HA epitope fused to the C-terminal end of the Malaria polypeptide and the other to the N-terminal end. In this way the Plasmodium proteome can be displayed on the surface of 96-well microtiter plates. The HisTAP method, system, and kit can be used instead of the HA-EpiTAP approach. Also, the T7 in vitro transcription/translation approach is one example of a system and method for expressing the genes, rather than a cell based system or in conjunction therewith.

Sera from individuals, immunized either by irradiated sporozoites or by natural exposure to Malaria, can be applied to the plates and antigen-bound antibody can be detected with alkaline phosphatase conjugated anti-human antibody. Skilled artisans will appreciate that the assay can be set up so that the level of intensity of the alkaline phosphatase signal will be proportional to the amount of antibody against a given antigen that is present in the serum.

For the Cellular Vaccine Antigen Scan (FIG. 7), TAP fragments (without the HA tag) encoding each of the Malaria antigens are individually amplified. Again, Malaria and the *P. falciparum* genome are used to illustrate application to one scenario. However, one of skill in the art will understand that the systems, methods, and kits can be applied to any organism or cell.

Described is an example protocol for scanning the plasmodium genome. One microgram of each fragment can be mixed with two micrograms of the GenePORTER transfection reagent and the mixture is transferred to 96-well plates containing haplotype specific antigen presenting cells. The transfection continues for 48 hours. These TAP transfected cells can serve as the target cells for the cellular immune assay, and can be transferred to standard ELIspot plates precoated with anti-IFN-γ (Th1 type response) or antil-IL-4 (Th2 type response) mAbs. T-cells from sporozoite immunized or naturally exposed individuals (effector cells) are transferred to each well containing the transfected antigen presenting cells, and are cultured for 24 hours, and subsequently processed as per a conventional ELIspot assay. The spot forming cells (SFCs) are enumerated using a computerized ELIspot counting machine. The number of cytokine producing cells indicates that the individual has T-cells directed against the TAP fragment that was transfected in the antigen presenting cells for that individual well. In addition, the supernatant from the cultures can be stored at −70° C. for assay by conventional cytokine ELISA assays, if necessary.

All of the gene specific primers used to generate EpiTAP fragments for the Humoral Vaccine Antigen Scan can be applicable for the generation of the TAP fragments required for the Cellular Vaccine Antigen Scan, so it is not necessary to generate any new primers. The complete genome can be scanned in period time that was impossible with traditional techniques. Further, multiple individuals can be screened who express different HLA alleles represented in high frequencies in most racial and ethnic populations (e.g. HLA-A2, A1, A3, B7).

The development of methods for utilizing genomic data to screen for candidate vaccine antigens can be limited by the ability to validate that the appropriate recall immune responses can be induced against identified targets. The present invention includes a system for monitoring T cell and antibody responses, which allows surveying of the cellular and humoral immune responses from Malaria exposed individuals in order to ensure adequate immune recall. Identification of the stage-specific expression of target antigens can be important. IFN-γ can be used as the primary marker of cellular immunogenicity because the protective immunity against pre-erythrocytic stage Malaria induced by immunization with irradiated sporozoites is mediated by IFN-γ. Professional antigen presenting cells can also be exploited, specifically HLA-transfected B cell lines. The screening assay can rely on the use of samples from immune volunteers who have been immunized with radiation-attenuated *P. falciparum* sporozoites or semi-immune individuals naturally exposed to Malaria, since the entire repertoire of protective T cell specificities will be represented in these individuals. The IFN-γ levels in the mixed cultured can be measured by using an Elispot assay, similar to that disclosed in Example 3 for the Vaccinia Virus.

Embodiments of the present invention include methods and systems for scanning the humoral and cellular immune responses against genes from *P. falciparum* genome for recognition by PBMCs and sera from immune individuals experimentally immunized with irradiated *P. falciparum* sporozoites or semi-immune individuals naturally exposed to Malaria. One outcome of this scan is the identification of those antigens that are expressed by irradiated sporozoites in hepatocytes (targets of protective T cell immune responses) and those antigens expressed by blood stage parasites (targets of protective antibody responses).

Developing a Subunit Vaccine, Pharmaceutical Composition, or Immunogenic Composition A particular peptide that has been identified to elicit either a humoral or cell-mediated immune response, can be further explored to determine its ability to be used in a subunit vaccine, pharmaceutical composition, or immunogenic composition. The terms "subunit vaccine," "pharmaceutical composition" and "immunogenic composition" encompass vaccines that are comprised of polypeptides, nucleic acids or a combination of both. Further exploration of a polypeptide candidate includes testing the polypeptide or nucleic acid encoding said polypeptide in a large percentage of patients. In a particular embodiment, surface antigens can be studied closely because of the likelihood that they can inhibit virus infectivity. In one embodiment, every polypeptide encoded by the Vaccinia genome is assayed to determine its immunogenic effect. Polypeptides that elicit an immune response, whether cell-mediated or humoral, can be more closely studied to determine potential use alone or in conjunction with other polypeptides and genes as a subunit vaccine, pharmaceutical composition, or immunogenic composition. Suitable methodologies for electing and detecting an immune response are well established in the art.

Other Target Organisms

While the above embodiment provides a detailed description for detecting the immunogenic response of Vaccinia polypeptides and developing subunit vaccines based on the results, a skilled artisan can appreciate that similar methods can be utilized for any particular target organism.

EXAMPLE 1

Procedure of Generating Histidine Tagged TAP Express Fragments

A detailed procedure that was used to produce tagged T7-TAP Express fragments is as follows: 96 different genes were amplified from a mixture of plasmid templates. A first PCR reaction was run with customized 5' and 3' primers. The 5' primers contained between 43–48 bases. In particular, the T-7-His TAP ends contained 28 bases while the gene-specific component contained between 15–20 bases. The 3' primers contained between 45–50 bases. Specifically, the T7-terminator TAP ends contained 30 bases while the gene specific component contained between 15–20 bases. The reaction temperature and times for the first PCR reaction were: 94° C. for 2 minutes, followed by 28 cycles of: 94° C. for 20 seconds, 58° C. for 35 seconds, and 70° C. for 2 minutes (for genes that contained more than 2 kb, 1 minute was added for each kb).

After the first PCR reaction was performed, an aliquot of each PCR reaction from the previous step was transferred into a PCR reaction containing the T7-histidine promoter fragment and T7 terminator fragment. The T7 promoter primer contained 25 bases, while the T7-promoter-His tag fragment contained a 104 base EcoRV/BglII fragment. The T7-terminator fragment was a 74 base oligonucleotide. The reaction temperature and times for the second PCR reaction were: 94° C. for 2 minutes, followed by 30 cycles of: 94° C. for 20 seconds, 60° C. for 35 seconds, and 70° C. for 2 minuets (for genes that contained more than 2 kb, 1 minute was added for each kb).

EXAMPLE 2

Using the Vaccinia Virus Proteome to Identify the Antigenic Targets of Humoral Immunity in Vaccinia Vaccinated Mice and Humans The following is a method used to systematically screen and identify all of the antigens in Vaccinia virus that give rise to a protective humoral immune response. Through the use of TAP technology every gene of the Vaccinia genome is amplified. The PCR reactions are performed such that a nucleotide sequence encoding an HA epitope is attached to these amplified transcriptionally active genes. The resulting HA-tagged TAP fragments are expressed to produce all 266 Vaccinia virus polypeptides containing the HA epitope tag. The 266 HA tagged polypeptides are placed in different HA-antibody coated wells in a 96-well plate. Serum from Vaccinia immunized humans is added to each of the 266 different wells. The reaction is incubated and washed to remove unbound serum polypeptides. Antibodies specific for the polypeptides attached to the plates remain bound to the plates. Enzyme linked anti-human antibody (for detecting polypeptide specific antibodies from human sera) is added to each well. The wells are incubated and washed to remove unbound antibody. A substrate is added to quantify the polypeptide specific antibody that is bound to the plate.

EXAMPLE 3

Using the Vaccinia Virus Proteome to Identify the Antigenic Targets of Cell-Mediated Immunity in Vaccinia Vaccinated Mice and Humans The following is a method that is used to systematically screen and identify all of the antigens in Vaccinia virus that give rise to a protective cell-mediated immune response. Through the use of TAP technology every gene of the Vaccinia genome is amplified. The PCR reactions are performed such that every gene becomes transcriptionally active. The resulting TAP fragments are expressed to produce all 266 Vaccinia virus polypeptides. Each of the polypeptides are delivered into dendritic cells, located in 96-well plates, using a polypeptide delivery reagent. Serum from Vaccinia immunized humans is added to each of the 266 different wells.

An IFN-γ ELISPOT assay is run using the following materials and method:

Materials:
Millipore 96-well multi-screen filtration plates (Millipore #MAIP S45-10) (Millipore, Bedford, Mass.)
Anti-IFN-g purified MAb (Clone 1-D1K) (MABTECH #3420-3) (Mabtech, Naka, Sweden) Anti-IFN-g Biotinylated MAb (Clone 7-B6-1) (MABTECH #3420-6) (Mabtech, Naka, Sweden)
Streptavidin-Alkaline Phosphatase (MABTECH #3310-8) (Mabtech, Naka, Sweden)
Alkaline Phosphate Substrate Kit (BIO-RAD #170-6432) (Bio-Rad, Hercules, Calif.)
Carbonate Buffer pH 9.6 (0.2 µM sterile filtered)
RPMI-1640 Medium (GIBCO #22400-089) (Gibco, Grand Island, N.Y.)
Fetal Bovine Serum (Sigma #F4135-500 mL) (Sigma, St. Louis, Mo.)
1×PBS (Prepared from 10×PBS DIGENE #3400-1010) (DIGENE, Gaithersburg, Md.)
Tween® 20 (J. T. Baker #X251-07) (J. T. Baker, Phillipsburg, N.J.)

Method:
96-well plates are coated with Coating Antibody (anti-IFN-g Clone 1-D1K) at 10–15 µg/nL (100 µL/well) and incubated at 4° C. overnight. Using aseptic technique, plates are flicked to remove Coating Antibody and washed 6 times with RPMI-1640. Plates are blocked with 100 µL/well of RPMI-1640+10% FBS (or Human AB serum) for 1–2 hours at room temperature. Plates are flicked to remove blocking buffer and 100 µL/well of antigen specific or control peptides are added at a final concentration of 10 µg/well. Peripheral blood lymphocytes (PBL) are added at 4×105/well and 1×105/well. Plates are incubated at 37° C./5% $CO_2$ for 36 hours. Plates are flicked to remove cells and washed 6 times with PBS+0.05% Tween® 20 at 200–250 µL/well. Plates are blot dried on paper towels.

Biotinylated antibody (anti-IFN-g Clone 7-B6-1) diluted 1:1,000 in 1×PBS at 100 µL/well is added. The resulting solution is incubated for 3 hours at room temperature. Plates are flicked to remove biotinylated antibody and washed 6 times with PBS+0.05% Tween® 20 at 200–250 µL/well. Plates are blot dried on paper towels. Streptavidin alkaline phosphatase is added at 100 µL/well diluted 1:1,000 in 1×PBS. The plates are incubated for 1 hour at room temperature. Plates are flicked to remove the streptavidin alkaline phosphatase and washed 6 times with 0.05% Tween® 20 at 200–250 µL/well. The plates are washed again 3 times with 1×PBS at 200–250 µL/well. The plates are blot dried on paper towels.

Substrate is added at 100 µL/well for 10–15 minutes at room temperature. The substrate is prepared according to manufacturer's protocol. The 25×substrate buffer is diluted in dH20 to a 1× concentration. Reagent A & B are each diluted 1:100 in the 1×substrate buffer. Rinsing plates with generous amounts of tap water (flooding plate and flicking several times) stops colorimetric substrate. Plates are allowed to dry overnight at room temperature in the dark. Spots corresponding to IFN-γ producing cells are determined visually using a stereomicroscope (Zeiss KS ELIspot). Results can be expressed as the number of IFN-γ-secreting cells per $10^6$ spleen cells. Responses are considered positive if the response to test Vaccinia peptide epitope is significantly different (p<0.05) as compared with the response to no peptide and if the stimulation index (SI=response with test peptide/response with control peptide) is greater than 2.0.

EXAMPLE 4

Cellular Vaccine Antigen Screen

A human volunteer was immunized with irradiated sporozoites from *P. falciparum*, the infectious agent responsible for Malaria. Dendritic cells from the volunteer were isolated and cultured. Recombinant CSP polypeptide from *P. falciparum* was delivered to dendritic cells with or without polypeptide delivery reagents described in U.S. patent application Ser. No. 09/738046, entitled "Intracellular Protein Delivery Reagent," which is hereby incorporated by reference in its entirety. T-cells isolated from the immunized volunteer were added to the cultures. The EliSpot assay identified 120 CSP antigen specific T-cells out of 250,000 T-cells that were added to the culture when CSP was added to the culture together with said delivery reagents. When CSP was added without said delivery reagents, the signal was barely above background.

EXAMPLE 5

DNA Immunization of Mice

Experiments are set up with five animals per group, consisting of four week old BALB/c female mice, averaging 40 animals per experiment. These mice are immunized IM in each tibialis anterior muscle with 50 µg plasmid DNA or transcriptionally active PCR fragment encoding selected Vaccinia virus antigens, 3 times at 3 week intervals.

Sera is collected 10 days after each immunization for antibody studies. Blood samples (~50 µl) are collected from the mice by orbital bleed with a sterilized pasture pipette. The mice are bled about once a week at a volume of approximately 50 µl.

Splenocytes are harvested at 14 days after the 3rd immunization and pooled for T-cell studies such as IFN-γ ELIspot assays. Tissue collections are done on animals euthanized via $CO_2$ (SOP 98.19) at the end of the experiment. The experiments can be five animals/group, averaging 40 animals/experiment×4 experiments for a total of 160 mice.

EXAMPLE 6

Preparation of Vaccinia Virus Genomic DNA to be Used as PCR Template

Vaccinia virion DNA is used as a PCR template. Crude-stock Vaccinia is used to infect 10 liters of HeLa cell spinner culture. 2–3 days after infection, cells are harvested by centrifugation and broken by ounce in 10 mM Tris-HCl (pH 9.0) on ice. Nuclei is pelleted, washed and re-pelleted after which supernatants are combined, trypsinized, and layered onto a 36% sucrose cushion. After centrifugation, the pelleted viruses are dispersed and trypsinized, and overlaid onto a continuous 5–40% sucrose gradient. Bands are collected, diluted and the virus is washed. A deoxycholate extract of the purified virions are centrifuged to remove debris, the pellet re-extracted, and the combined supernatants applied to a DEAE cellulose column, equilibrated in 0.1 M KCl., Tris-HCl pH 8.4. After washing the column with 250 mM KCl, Vaccinia DNA is eluted with 0.7 M KCl, ethanol precipitated and redissolved in TE buffer.

EXAMPLE 7

Preparation of Human Dendritic Cells

Dendritic cells were ordered from Allcells: Cat #PB002 (NPB-Mononuclear Cells). The cells were in 50 mL buffer. The cells were counted immediately, the total number was $312.5 \times 10^6$. The cells were pelleted, and resuspended in 25 mL RPMI-1640 containing DNAse. This solution (30 µg /mL) was incubated for 5 minutes at room temperature. The cells were washed twice with complete medium. The cells were resuspended at $10 \times 10^6$ cells/3 mL. Twelve 10 mm dishes containing 10 mL complete medium in each dish were used. The cells were incubated at 37° C. for 3 hours. The non-adherent cells were removed by gently shaking plates and aspirating supernatant. Afterwards, the dishes containing adherent cells were washed 3 times with 10 mL of RPMI-1640 containing 2% Human Serum. 10 mL of culture medium were added to each plate containing 50 ng/mL GM-CSF and 500 u/mL IL-4. This culture medium was added until day 4. After day 4, culture medium without GM-CSF and IL-4 was added. The transfection was done on day 5. The complete medium consisted of RPMI-1640 (455 mL), 5% Human AB Serum (25 mL), Non-essential Amino Acids (5 mL), Sodium Pyruvate (5 mL), L-Glutamine (5 mL), and Penicillin-Streptomycin (5 mL).

EXAMPLE 8

Generation of Dendritic Cells from Mouse Bone Marrow

Cells were taken from the bones of one mouse (2 femur and 2 tibiae without removing the macrophages). The red blood cells were obtained from the bone marrow and lysed. The cells were counted ($51 \times 10^6$ cells, total) and cultured in a growth medium ($2.5 \times 10^6$ cells/plate, 10 mL/plate) for 8 days before transfection. On day 4 another 10 mL of growth medium was added. On day 6, 10 mL of the old medium was taken from each plate and the cells were pelleted. The cells were resuspended in 10 mL medium with 10 ng/mL GM-CSF and 2.5 ng/mL IL-4. The cells were placed back into the culture. The cells were cultured until transfection on day 8. On the day of transfection, $2.5 \times 10^6$ cells were harvested from each dish. The growth medium for mbmDC contained DMEM/Iscove, 10% FCS, 50 uM β-mercaptoethanol, 1×Penicillin/Streptomycin, 2 mM L-Glutamine, 10 mM Hepes, 1×Non-essential amino acids, 20 ng/mL rmGM-CSF, and 5 ng/mL rmIL-4.

EXAMPLE 9

Adding an HA Epitope Tag

Oligos are designed using TAP promoter and terminator fragments from pCMVm and pTP-SV40, respectively, and adding the nucleotide sequence encoding the HA epitope tag. For adding the HA epitope to the 5' end of the coding sequence the following sequences is used:

```
Promoter 5':
CCGCCATGTTGACATTG                            (SEQ ID NO:2)

Promoter 3':
GGCAGATCTGGGAGGCTAGCGTAATCCGGAACATCGT        (SEQ ID NO:3)
     ATGGGTACATTGTTAAGTCGACGGTGC
```

For adding the HA epitope to the 3' end of the coding sequence, the following sequences is used:

```
Terminator 5':
GATCCCGGGTACCCATACGATGTTCCGGATTACGCTT        (SEQ ID NO:4)
          AGGGGAGATCTCAGACATG Terminator 3':
CAGGATATCATGCCTGCAGGACGACTCTAGAG             (SEQ ID NO:5)
```

The Method Includes:

PCR is used to amplify a new HA-promoter utilizing pCMVm as a template and a new HA-terminator utilizing pTP-SV40 as a template. The resulting PCR products are gel purified using QIAGEN QIAquick Gel Extraction Kit (Qiagen, Seattle, Wash.). The PCR products and both plasmids (pCMVm & pTP-SV40) are digested with EcoRV and BglII restriction enzymes. All digested products are gel purified using QIAquick Gel Extraction Kit. The HA-promoter and HA-terminator are ligated separately into the digested pCMVm and pTP-SV40 plasmids. These plasmids are transformed into DH5, grown overnight on LB plates containing Kanamycin, colonies are selected and grown in LB media containing Kanamycin. QIAGEN QIAprep Spin Miniprep Kit is used to isolate plasmids. Plasmids are digested using EcoRV and BglII. Digests are run on a gel to identify clones containing plasmid with insert of correct size. The plasmids are sequenced to confirm inserts are correct. A prep culture is grown, plasmids are isolated, plasmids are digested with EcoRV and BglII, and promoter and terminator fragments are gel purified. Epi-TAP-5'HA and Epi-TAP-3'HA kits are used.

What is claimed is:

1. A method of screening a library of target organism polypeptides in order to identify a target organism antigen that is capable of eliciting a humoral immune response, comprising:
   (a) providing a library of target organism polypeptides attached to a linker molecule, wherein the library is generated according to a method comprising the steps of:
      (i) providing a desired polynucleotide sequence from a target organism and a first primer pair capable of amplifying the desired polynucleotide sequence;
      (ii) performing a first PCR reaction using the first primer pair and the desired polynucleotide sequence, thereby generating an amplified coding sequence, wherein the amplified coding sequence is not transcriptionally active;
      (iii) adding at least one polynucleotide sequence operably encoding a linker molecule to the amplified coding sequence, thereby generating an amplified coding sequence-linker polynucleotide;
      (iv) providing a second primer pair capable of adding at least one nucleotide sequence that confers transcriptional activity to the amplified coding sequence-linker polynucleotide;
      (v) performing a second PCR reaction wit the second primer pair and the amplified coding sequence-linker polynucleotide, thereby generating a transcriptionally active coding sequence-tinker polynucleotide;
      (vi) expressing a polypeptide from the transcriptionally active coding sequence-linker polynucleotide, wherein expressing the polynucleotide produces a target organism polypeptide attached to a linker molecule; and
      (vii) repeating steps (i)–(vi) at least 10 times, with different first primer pairs to express different polypeptides of said target organism, thereby generating a library of target organism polypeptides attached to a linker molecule;
   (b) immobilizing at least 10 of the target organism polypeptides attached to a linker molecule from the library to a solid support, wherein the linker molecule immobilizes the target organism polypeptide to the solid support; and
   (c) assaying the target organism polypeptides immobilized to the solid support with at least one antibody from an animal that has been immunized with one or more antigens from the target organism, thereby screening a library of target organism polypeptides in order to identify a target organism antigen that is capable of eliciting a humoral immune response.

2. The method of claim 1, wherein the target organism is Vaccinia virus.

3. The method of claim 1, wherein the target organism is *Mycobacterium tubereculosis*.

4. A method of screening a library of target organism polypeptides in order to identify a target organism antigen that is capable of eliciting a humoral immune response, comprising:
   (a) providing a library of target organism polypeptides attached to a linker molecule, wherein the library is generated according to a method comprising the steps of:
      (i) providing a desired polynucleotide sequence from a target organism and a first primer pair capable of amplifying the desired polynucleotide sequence;
      (ii) performing a first PCR reaction using the first primer pair and the desired polynucleotide sequence, thereby generating an amplified coding sequence, wherein the amplified coding sequence is not transcriptionally active;
      (iii) providing a second primer pair capable of adding at least one nucleotide sequence that confers transcriptional activity to the amplified coding sequence;
      (iv) performing a second PCR reaction with the second primer pair and the amplified coding sequence, thereby generating a transcriptionally active coding sequence;
      (v) adding at least one polynucleotide sequence operably encoding a linker molecule to the transcriptionally active coding sequence, thereby generating a transcriptionally active coding sequence-linker polynucleotide;
      (vi) expressing a polypeptide from the transcriptionally active coding sequence-linker polynucleotide, wherein expressing the polypeptide produces a target organism polypeptide attached to a linker molecule; and
      (vii) repeating steps (i)–(vi) at least 10 times, with different first primer pairs to express different polypeptides of said target organism, thereby generating a library of target organism polypeptides attached to linker molecule;
   (b) immobilizing at least 10 of the target organism polypeptides attached to a linker molecule from the library to a solid support, wherein the linker molecule immobilizes the target organism polypeptide to the solid support; and
   (c) assaying the target organism polypeptides immobilized to the solid support with at least one antibody from an animal that has been immunized with one or more antigens from the target organism, thereby screening a library of target organism polypeptides in order to identity a target organism antigen that is capable of eliciting a humoral immune response.

5. The method of claim 4, wherein the target organism is Vaccinia virus.

6. The method of claim 4, wherein the target organism is *Mycobacterium tubereculosis*.

7. A method of screening an array of target organism polypeptides in order to identify a target organism antigen that is capable of eliciting a humoral immune response, comprising:
- (a) providing an may of at least 20 target organism polypeptides attached to a linker molecule, wherein the array is prepared according to a method comprising the steps of:
  - (i) providing a desired polynucleotide sequence from a target organism and a first primer pair capable of amplifying the desired polynucleotide sequence;
  - (ii) performing a first PCR reaction using the first primer pair and the desired polynucleotide sequence from the target organism, thereby generating an amplified coding sequence, wherein the amplified coding sequence is not transcriptionally active;
  - (iii) adding at least one polynucleotide sequence operably encoding a linker molecule to the amplified coding sequence, thereby generating an amplified coding sequence-linker polynucleotide;
  - (iv) providing a second primer pair capable of adding at least one nucleotide sequence that confers transcriptional activity to the amplified coding sequence-linker polynucleotide;
  - (v) performing a second PCR reaction with the second primer pair and the amplified coding sequence-linker polynucleotide, thereby generating a transcriptionally active coding sequence;
  - (vi) expressing to polypeptide from the transcriptionally active coding sequence, wherein expressing the polypeptide produces a target organism polypeptide attached to a linker molecule; and
  - (vii) repeating steps (i)–(vi) at least 20 times, with different first primer pairs to express different polypeptides of said target organism, wherein each polypeptide is placed in different location, thereby generating an array of at least 20 target organism polypeptides;
- (b) immobilizing at least 10 of the target organism polypeptides from the array to a solid support, wherein the linker molecule immobilizes the target organism polypeptide to the solid support; and
- (c) assaying the polypeptides with at least one antibody from an animal that has been immunized with one or more antigens from the target organism, thereby screening an array of target organism polypeptides in order to identify a target organism antigen that is capable of eliciting a humoral immune response.

8. The method of claim 7, wherein the target organism is Vaccinia virus.

9. The method of claim 7, wherein the target organism is *Mycobacterium tubereculosis*.

10. A method of screening an array of target organism polypeptides in order to identify a target organism antigen that is capable of eliciting a humoral immune response, comprising:
- (a) providing an array of at least 20 target organism polypeptides attached to a linker molecule, wherein the array is prepared according to a method comprising the steps of:
  - (i) providing a desired polynucleotide sequence from a target organism and a first primer pair capable of amplifying the desired polynucleotide sequence;
  - (ii) performing a first PCR reaction using the first primer pair and the desired polynucleotide sequence from the target organism, thereby generating an amplified coding sequence, wherein the amplified coding sequence is not transcriptionally active;
  - (iii) providing a second primer pair capable of adding at least one nucleotide sequence that confers transcriptional activity to the amplified coding sequence;
  - (iv) performing a second PCR reaction with the second primer pair and the amplified coding sequence, thereby generating a transcriptionally active coding sequence;
  - (v) adding at least one polynucleotide sequence operably encoding a linker molecule to the transcriptionally active coding sequence, thereby generating a transcriptionally active coding sequence-linker polynucleotide;
  - (vi) expressing the polypeptide from the transcriptionally active coding sequence-linker polynucleotide; wherein expressing the polypeptide produces a target organism polypeptide attached to a linker molecule; and
  - (vii) repeating steps (i)–(vi) at least 20 times, with different first primer pairs to express different polypeptides of said target organism, wherein each polypeptide is placed in different location, thereby generating an array of at least 20 target organism polypeptides;
- (b) immobilizing at least 10 of the target organism polypeptides from the array to a solid support, wherein the linker molecule immobilizes the target organism polypeptide to the solid support; and
- (c) assaying the polypeptides with at least one antibody from an animal that has been immunized with one or more antigens from a target organism, thereby screening an array of target organism polypeptides in order to identify a target organism antigen that is capable of eliciting a humoral immune response.

11. The method of claim 10, wherein the target organism is Vaccinia virus.

12. The method of claim 10, wherein the target organism is *Mycobacterium tuberculosis*.

13. A method of screening a library of target organism polypeptides in order to identify a target organism antigen that is capable of eliciting a humoral immune response, comprising:
- (a) providing a library of target organism polypeptides attached to a linker molecule, wherein the library is prepared according to a method comprising the steps of:
  - (i) providing a desired nucleic acid coding sequence from a target organism;
  - (ii) adding at least one polynucleotide sequence operably encoding a linker molecule to the nucleic acid coding sequence from the target organism, thereby generating a coding sequence-linker polynucleotide;
  - (iii) PCR cloning the coding sequence-linker polynucleotide into a vector according to a method comprising the steps of:
    - (1) flanking the coding sequence-linker polynucleotide with first and second adapter sequences, wherein the first and second adapter sequences are added by PCR, thereby generating an adapter-flanked coding sequence-linker polynucleotide; and
    - (2) contacting the adapter-flanked coding sequence-linker polynucleotide with a vector, wherein the vector comprises sequences homologous to the first and second adapter sequences, wherein the contacting step is performed within a host cell and the coding sequence-linker polynucleotide is incorporated into the vector by in vivo recombination in the host cell;

(iv) expressing a polypeptide from the coding sequence-linker polynucleotide, wherein expressing the polypeptide produces a target organism polynucleotide attached to a linker molecule; and (v) repeating steps (i)–(iv) at least 10 times, with different coding sequences to express different polypeptides of said target organism attached to a linker molecule, thereby generating a library of target organism polypeptides attached to a linker molecule;

(b) immobilizing at least 10 of the target organism polypeptides from the library to a solid support, wherein the linker molecule immobilizes the target organism polypeptide to the solid support, and (c) assaying the polypeptides with at least one antibody from an animal that has been immunized with one or more antigens from the target organism, thereby screening a library of target organism polypeptides in order to identify a target organism antigen that is capable of eliciting a humoral immune response.

14. The method of claim 13, wherein the target organism is *Mycobacterium tuberculosis*.

15. The method of claim 13, wherein the target organism is Vaccinia virus.

16. A method of screening a library of target organism polypeptides in order to identify a target organism antigen that is capable of eliciting a humoral immune response, comprising:

assaying said target organism polypeptides with at least one antibody from an animal that has been immunized with one or more antigens from the target organism, wherein, at least ten of the target organism polypeptides are attached to a solid support by a linker molecule, said target organism polypeptides drawn from a library of target organism polypeptides generated according to a method comprising the steps of:

(a) performing a first PCR reaction using a first primer pair and a desired polynucleotide sequence from a target organism, wherein said first primer is capable of amplifying the desired polynucleotide sequence, thereby generating an amplified coding sequence, wherein the amplified coding sequence is not transcriptionally active;

(b) adding at least one polynucleotide sequence encoding a linker molecule to the amplified coding sequence, thereby generating an amplified coding sequence-linker polynucleotide;

(c) performing a second PCR reaction with a second primer pair, wherein said second primer pair is capable of adding at least one nucleotide sequence that confers transcriptional activity to the amplified coding sequence-linker polynucleotide, thereby generating a transcriptionally active coding sequence-linker polynucleotide;

(d) expressing a polypeptide from the transcriptionally active coding sequence-linker polynucleotide, wherein expressing the polypeptide produces a target organism polypeptide attached to a linker molecule; and (e) repeating steps (a)–(d) at least 10 times, with different first primer pairs to express different polypeptides of said target organism, thereby generating a library of target organism polypeptides attached to a linker molecule;

thereby screening a library of target organism polypeptides in order to identify a target organism antigen that is capable of eliciting a humoral immune response.

17. The method of claim 16, wherein the target organism is Vaccinia virus.

18. The method of claim 16, wherein the target organism is *Mycobacterium tuberculosis*.

* * * * *

UNITED STATES PATENT AND TRADEMARK OFFICE
CERTIFICATE OF CORRECTION

| | | |
|---|---|---|
| PATENT NO. | : 7,319,012 B2 | Page 1 of 4 |
| APPLICATION NO. | : 10/159428 | |
| DATED | : January 15, 2008 | |
| INVENTOR(S) | : Felgner et al. | |

It is certified that error appears in the above-identified patent and that said Letters Patent is hereby corrected as shown below:

Title Page item 56

At Column 2, Page 1, line 24, under Other Publications, delete "Methoanogenic" and insert -- Methanogenic --, therefor.

At Column 2, Page 2, line 5, under Other Publications, delete "homebox" and insert -- homeobox --, therefor.

At Column 2, Page 2, line 15, under Other Publications, delete "fro" and insert -- from --, therefor.

At Column 2, Page 2, line 17, under Other Publications, delete "1776" and insert -- 1766 --, therefor.

At Column 2, Page 2, line 20, under Other Publications, delete "Recurvise" and insert -- Recursive --, therefor.

At Column 2, Page 2, line 31, under Other Publications, delete "Exherichia" and insert -- Escherichia --, therefor.

At Column 2, Page 2, line 33, under Other Publications, delete "Eschenichia" and insert -- Escherichia --, therefor.

In the Drawings

At Sheet 2 of 11, Figure 2, line 6, delete "unversal" and insert -- universal --, therefor.

At Column 7, line 24, after "response" insert -- . --.

At Column 12, lines 56-57, delete "Additionaly," and insert -- Additionally, --, therefor.

UNITED STATES PATENT AND TRADEMARK OFFICE
CERTIFICATE OF CORRECTION

| | |
|---|---|
| PATENT NO. | : 7,319,012 B2 |
| APPLICATION NO. | : 10/159428 |
| DATED | : January 15, 2008 |
| INVENTOR(S) | : Felgner et al. |

It is certified that error appears in the above-identified patent and that said Letters Patent is hereby corrected as shown below:

At Column 15, line 34, delete "availabe" and insert -- available --, therefor.

At Column 17, line 7, delete "neplastic" and insert -- neoplastic --, therefor.

At Column 18, line 58, delete "02/123,34" and insert -- 02/12334 --, therefor.

At Column 19, lines 20-27, below "element." delete "The vector can.......selection element.".

At Column 19, line 31, delete "DH %," and insert -- DH% --, therefor.

At Column 27, line 16, before "capable" delete "is".

At Column 27, line 42, delete "EliSpot" and insert -- ELIspot --, therefor.

At Column 27, line 67, delete "Sterptavidin" and insert -- Streptavidin --, therefor.

At Column 28, line 16, delete "T cell" and insert -- T-cell --, therefor.

At Column 29, line 50, delete "T cell" and insert -- T-cell --, therefor.

At Column 30, line 16, delete "HA-Epitope" and insert -- HA Epitiope --, therefor.

At Column 30, line 53, delete "HA-epitope" and insert -- HA epitiope --, therefor.

At Column 31, line 46, delete "T cell" and insert -- T-cell --, therefor.

At Column 31, line 61, delete "T cell" and insert -- T-cell --, therefor.

At Column 32, line 6, delete "T cell" and insert -- T-cell --, therefor.

At Column 34, line 10, delete "μg/nL" and insert -- μg/mL --, therefor.

At Column 34, line 39, delete "dH20" and insert -- dH$_2$O --, therefor.

At Column 34, line 64, delete "09/738046" and insert -- 09/738,046 --, therefor.

UNITED STATES PATENT AND TRADEMARK OFFICE
CERTIFICATE OF CORRECTION

| | |
|---|---|
| PATENT NO. | : 7,319,012 B2 |
| APPLICATION NO. | : 10/159428 |
| DATED | : January 15, 2008 |
| INVENTOR(S) | : Felgner et al. |

It is certified that error appears in the above-identified patent and that said Letters Patent is hereby corrected as shown below:

At Column 34, line 67, delete "EliSpot" and insert -- ELIspot --, therefor.

At Column 39, line 37, in Claim 1, delete "wit" and insert -- with --, therefor.

At Column 39, line 40, in Claim 1, delete "tinker" and insert -- linker --, therefor.

At Column 39, line 67, in Claim 3, delete "tubereculosis" and insert -- tuberculosis --, therefor.

At Column 40, line 62, in Claim 4, delete "identity" and insert -- identify --, therefor.

At Column 40, line 67, in Claim 6, delete "tubereculosis" and insert -- tuberculosis --, therefor.

At Column 41, line 5, in Claim 7, delete "may" and insert -- array --, therefor.

At Column 41, line 29, in Claim 7, delete "to" and insert -- the --, therefor.

At Column 41, line 52, in Claim 9, delete "tubereculosis" and insert -- tuberculosis --, therefor.

At Column 42, line 16, in Claim 10, delete "polynucleotide;" and insert -- polynucleotide, --, therefor.

At Column 43, line 17, in Claim 13, delete "support," and insert -- support; --, therefor.

At Column 43, line 35, in Claim 16, delete "wherein" and insert -- whereby --, therefor.

UNITED STATES PATENT AND TRADEMARK OFFICE
CERTIFICATE OF CORRECTION

PATENT NO. : 7,319,012 B2
APPLICATION NO. : 10/159428
DATED : January 15, 2008
INVENTOR(S) : Felgner et al.

It is certified that error appears in the above-identified patent and that said Letters Patent is hereby corrected as shown below:

At Column 44, line 3, in Claim 16, after "primer" insert -- pair --, therefor.

Signed and Sealed this

Tenth Day of November, 2009

David J. Kappos
*Director of the United States Patent and Trademark Office*